(12) United States Patent
Moerman

(10) Patent No.: US 8,718,943 B2
(45) Date of Patent: May 6, 2014

(54) METHOD AND DEVICE FOR UTILIZING ANALYTE LEVELS TO ASSIST IN THE TREATMENT OF DIABETES

(75) Inventor: Piet Moerman, St. Martens-Latem (BE)

(73) Assignee: Abbott Diabetes Care Inc., Alameda, CA (US)

( * ) Notice: Subject to any disclaimer, the term of this patent is extended or adjusted under 35 U.S.C. 154(b) by 891 days.

(21) Appl. No.: 11/528,997

(22) Filed: Sep. 28, 2006

(65) Prior Publication Data

US 2007/0083335 A1 Apr. 12, 2007

Related U.S. Application Data

(63) Continuation-in-part of application No. 10/817,211, filed on Apr. 1, 2004, now abandoned.

(60) Provisional application No. 60/459,310, filed on Apr. 1, 2003.

(51) Int. Cl.
*G01N 33/48* (2006.01)
*G01N 31/00* (2006.01)
*G06G 7/48* (2006.01)
*G06G 7/58* (2006.01)

(52) U.S. Cl.
USPC ............... 702/19; 702/22; 703/11; 703/12

(58) Field of Classification Search
CPC .............. A61M 5/1723; A61M 2230/201; A61B 5/14532; G06F 19/3456
See application file for complete search history.

(56) References Cited

U.S. PATENT DOCUMENTS

| | | | |
|---|---|---|---|
| 5,507,288 A | 4/1996 | Bocker et al. | |
| 5,613,978 A | 3/1997 | Harding | |
| 6,024,699 A | 2/2000 | Surwit et al. | |
| 6,572,542 B1 * | 6/2003 | Houben et al. | 600/300 |
| 7,766,829 B2 | 8/2010 | Sloan et al. | |
| 2002/0060247 A1 | 5/2002 | Krishnaswamy et al. | |
| 2003/0068666 A1 | 4/2003 | Zweig | |
| 2003/0187338 A1 | 10/2003 | Say et al. | |
| 2004/0093167 A1 | 5/2004 | Braig et al. | |

(Continued)

FOREIGN PATENT DOCUMENTS

| | | |
|---|---|---|
| EP | 1225448 | 7/2002 |
| WO | WO-01/93743 A2 | 12/2001 |
| WO | WO-02/05702 A2 | 1/2002 |

OTHER PUBLICATIONS

International Preliminary Report on Patentability for Application No. PCT/IB2007/004347, dated Mar. 31, 2009, 4 pages.

(Continued)

*Primary Examiner* — Larry D Riggs, II
(74) *Attorney, Agent, or Firm* — Edward J. Baba; Michael B. Rubin; Bozicevic, Field & Francis LLP

(57) ABSTRACT

A health-monitoring device assesses the health of a user based on levels of two analytes in a biological fluid. A first analyte that is utilized to assess a user's health is a fat metabolism analyte, such as ketones, free fatty acids and glycerol, which is indicative of fat metabolism. A second analyte that is utilized is a glucose metabolism analyte, such as glucose. The levels of the two analytes may be used to assess insulin sensitivity, to detect both recent hypoglycemia and the cause of high glucose levels, and/or to guide therapeutic intervention.

33 Claims, 22 Drawing Sheets

(56) References Cited

U.S. PATENT DOCUMENTS

| | | |
|---|---|---|
| 2004/0180810 A1 | 9/2004 | Pilarski |
| 2004/0248204 A1 | 12/2004 | Moerman |
| 2009/0177068 A1 | 7/2009 | Stivoric et al. |

OTHER PUBLICATIONS

Belfort, Renata et al., "Dose-Response Effect of Elevated Plasma Free Fatty Acid on Insulin Signaling," *Diabetes*, vol. 54:1640-1648 (2005).

Boden, Guenther et al., "Mechanisms of Fatty Acid-induced Inhibition of Glucose Uptake," *J. Clin. Invest.*, vol. 93:2438-2446 (1994).

Bonadonna, R.C. et al., "Glucose and fatty acid metabolism in human obesity. Relationships to insulin resistance," *Diabetes Reviews*, vol. 5:21-51 (1997).

Crane, Marilyn L., "Role of Blood Ketone Testing in Sick-Day Management," *Managed Care*, vol. 13(4 Suppl.):11-14 (2004).

International Search Report for Application No. PCT/IB2007/004347, dated Jul. 18, 2008, 11 pages.

Moerman, Piet, "Utility of testing FFA levels in Type II and Type I diabetic patients," Innovative Metabolic Devices, Physiology FFA and Ketones (2007).

Freckmann et al., "Recent advances in continous glucose monitoring," Experimental Clinical Endocrinological Diabetes, vol. 109, Supplement 2, pp. S347-S357 (2001).

Laffel, "Ketone Bodies: a Review of Physiology, Pathophysiology and Application of Monitoring to Diabetes," Diabetes/Metabolism Research and Reviews, vol. 15, pp. 412-426 (1999).

Pinhas-Hamiel et al., "The Type 2 Family," Archives of Pediatrics & Adolescent Medicine, vol. 153, pp. 1063-1067 (1999).

\* cited by examiner

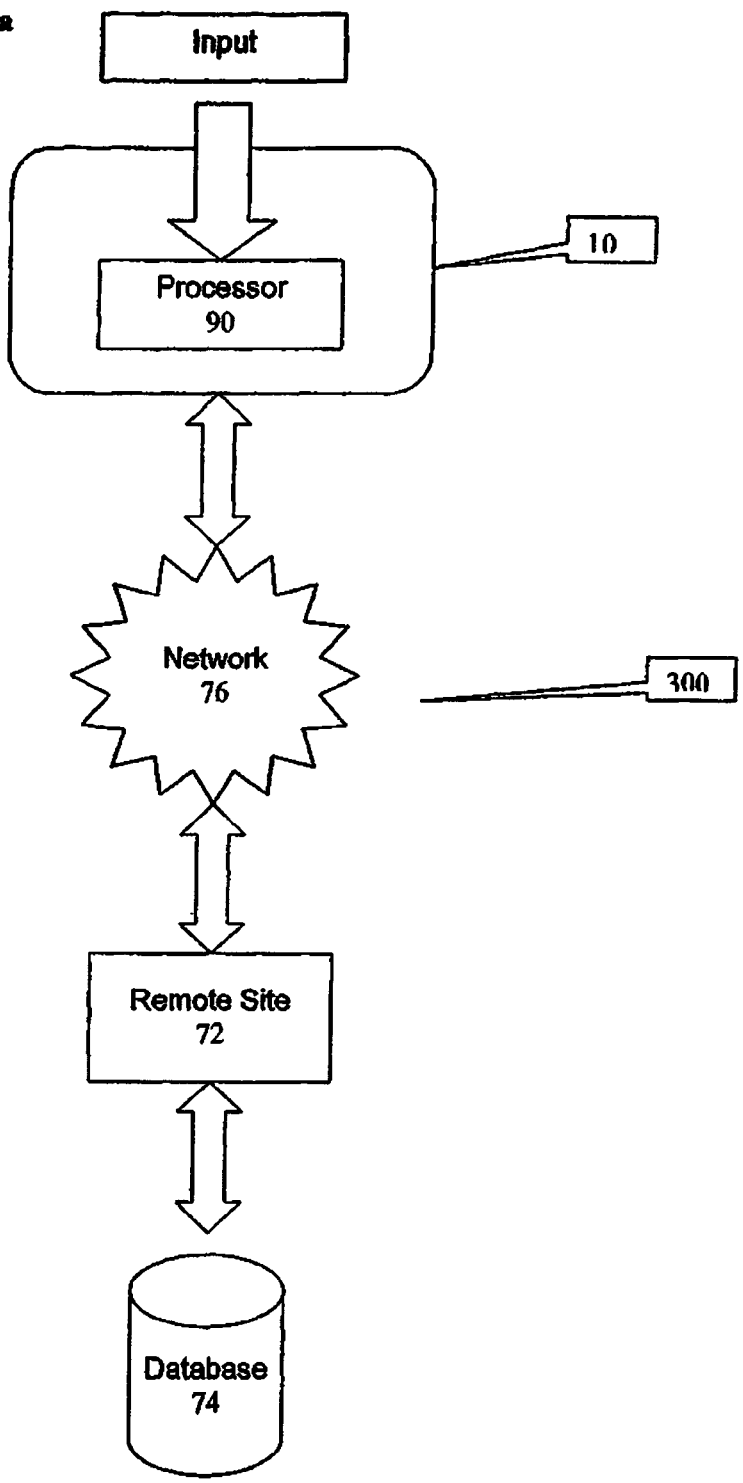
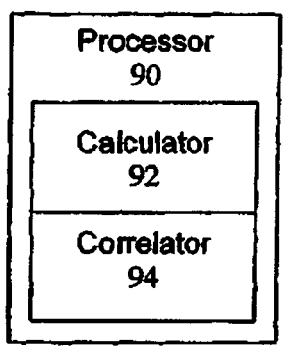

— Glucose Prediction Error (GPE): Error between measured and predicted glucose
······ Insulin Activity Error (IAE): Deviation FFA from expected theoretical insulin activity
▌ Unexpected (unpredicted) hypoglycaemia
▒ Predicted hypoglycaemia Figure 9
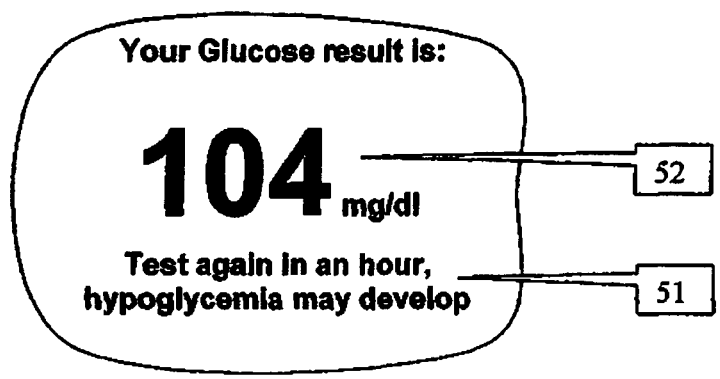
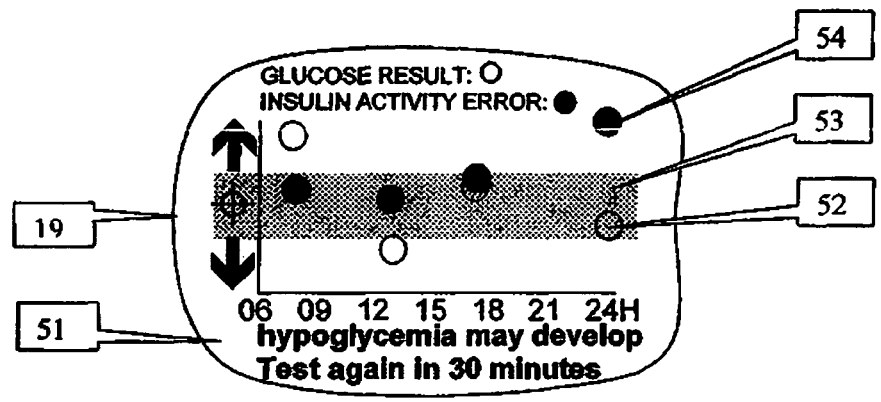
FIGURE 10

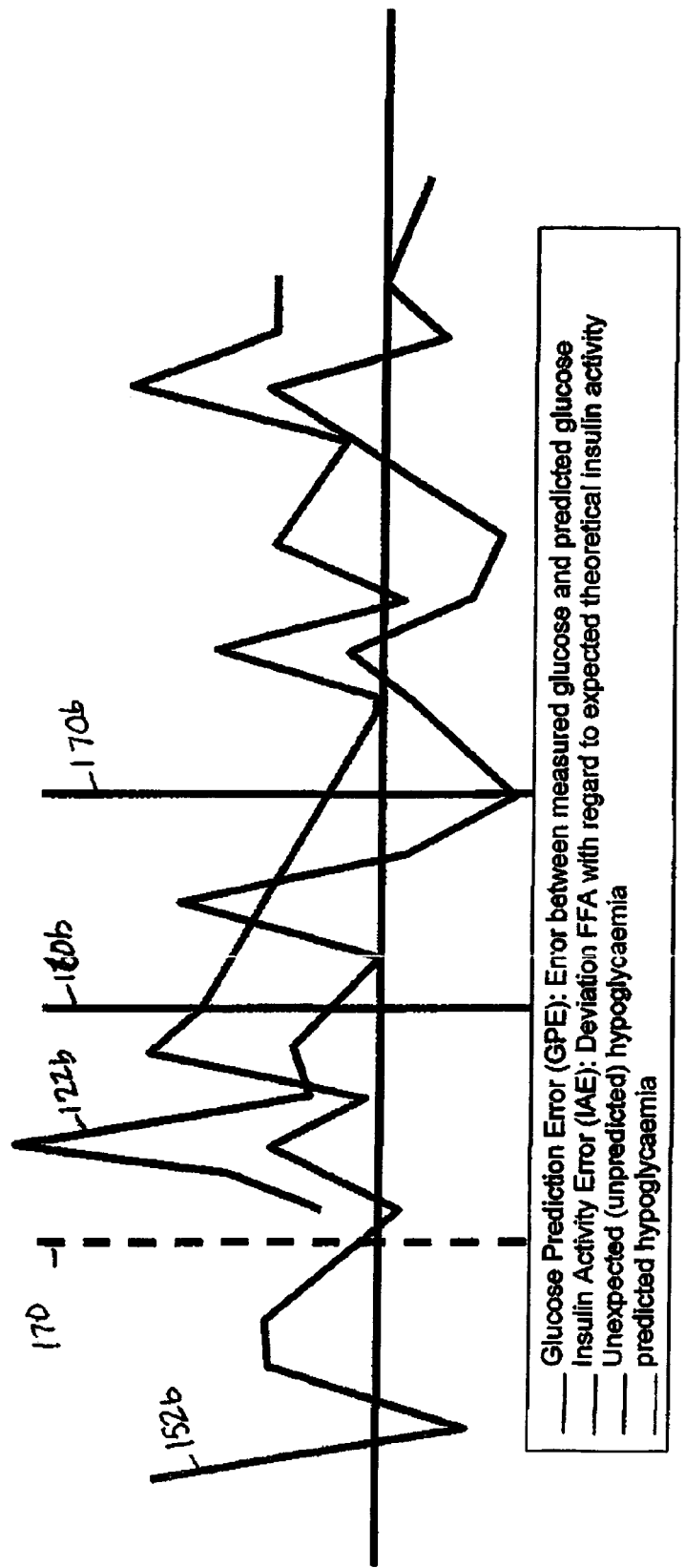

KP2 Ins Act

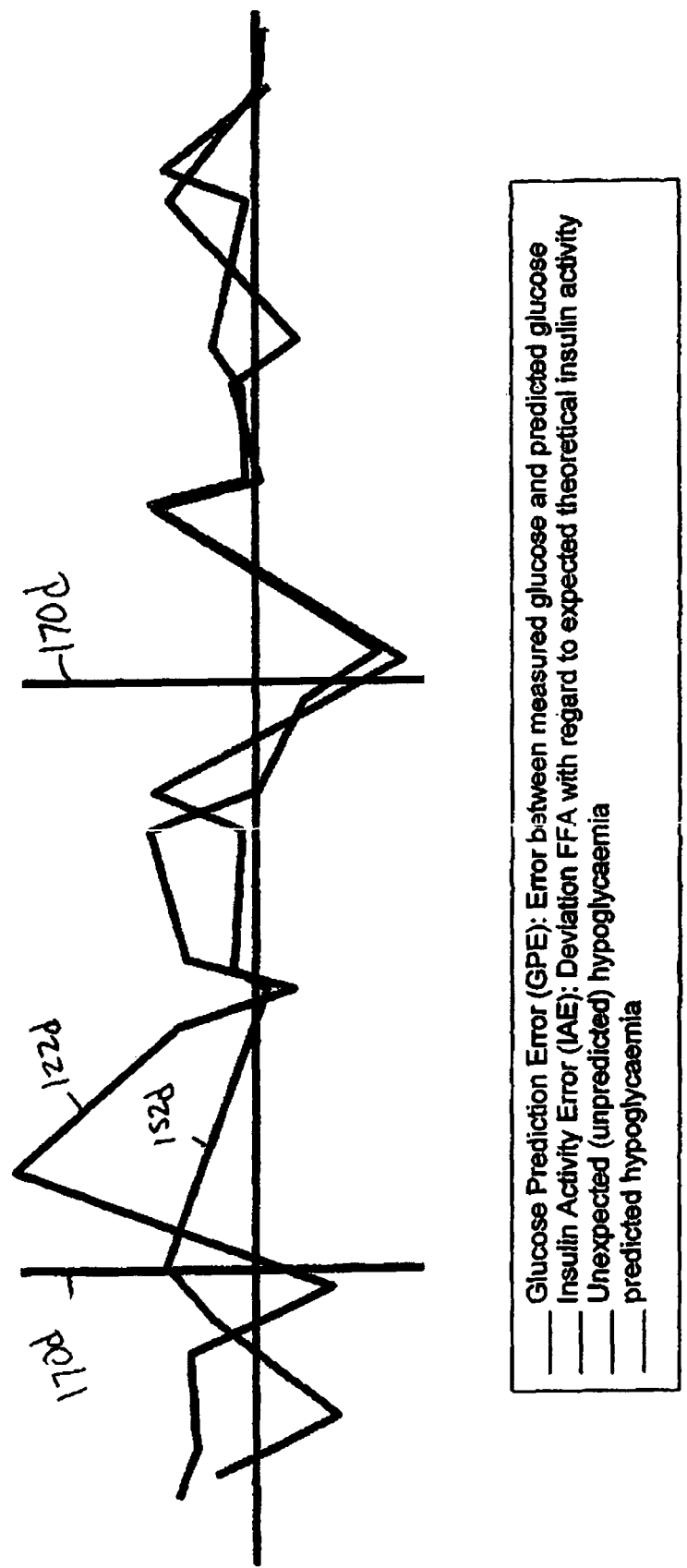

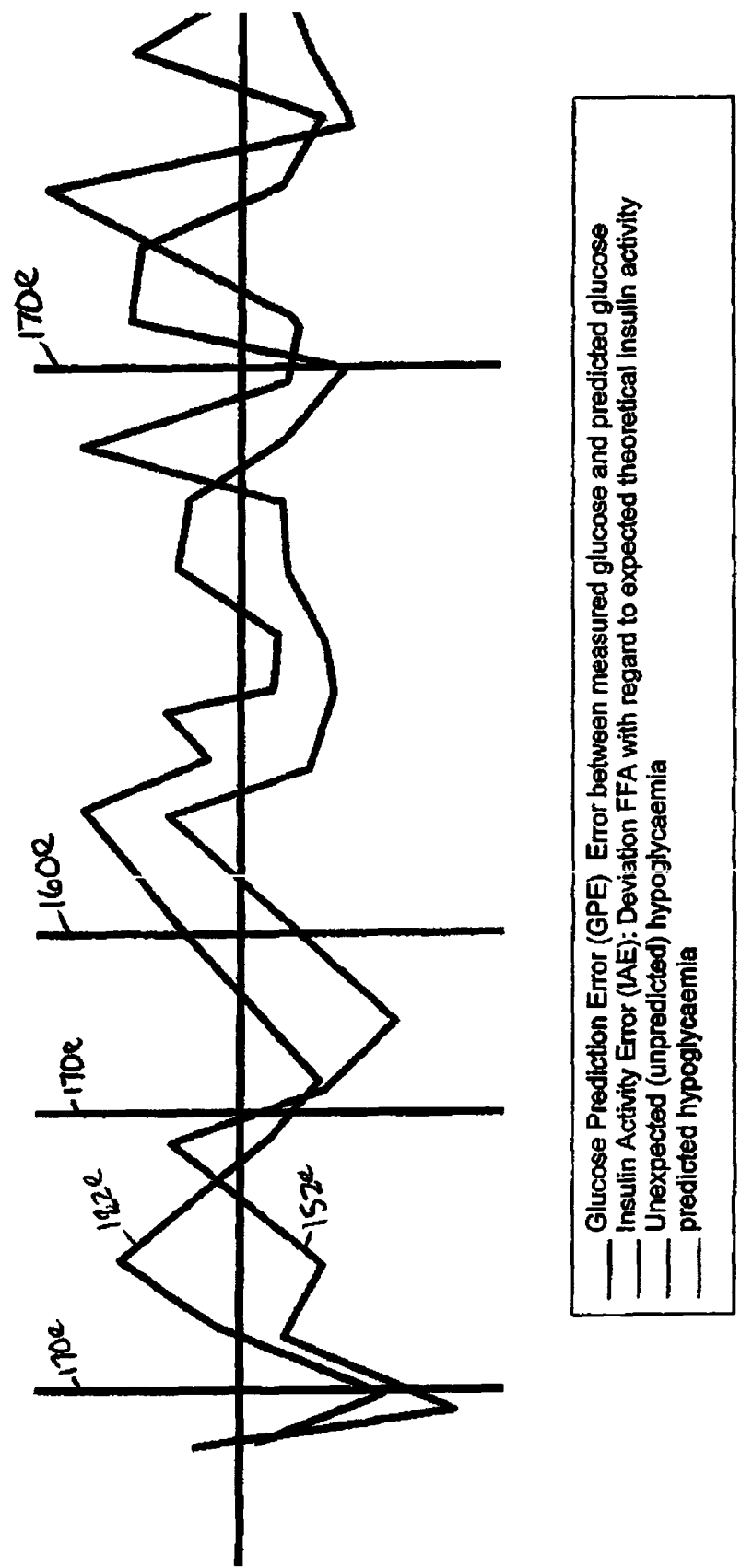

METHOD AND DEVICE FOR UTILIZING ANALYTE LEVELS TO ASSIST IN THE TREATMENT OF DIABETES

RELATED APPLICATIONS

The present invention is a continuation in part of U.S. patent application Ser. No. 10/817,211 filed Apr. 1, 2004, entitled Method and Device for Utilizing Analyte Levels to Assist in the Treatment of Diabetes, Insulin Resistance and Metabolic Syndrome, which in turn claims priority to U.S. Provisional Patent Application 60/459,310 entitled Method and Device for Utilizing Analyte Levels to Assist in the Treatment of Diabetes, Insulin Resistance and Metabolic Syndrome, filed Apr. 1, 2003, the contents of both of which are herein incorporated by reference.

FIELD OF THE INVENTION

The present invention relates to the management of metabolic syndrome and diabetes. More particularly, the present invention relates to methods for managing therapeutic interventions in diabetes using quantification of biochemical markers in the subject to assess the fat and glucose metabolism, insulin sensitivity as well as the past and prospective effects of a certain given medication.

BACKGROUND OF THE INVENTION

Between 1990 and 1998 the prevalence of diabetes in the United States rose from 4.9 to 6.5%. During the 1990's the prevalence of non-insulin dependent diabetes increased by 33% overall and by 70% among people in their thirties. Diabetes affects now sixteen million Americans. The direct costs resulting from diabetes is $44 billion per year, and the total cost of diabetes, including indirect costs, rises to $98 billion per year. 13.5% of obese patients have diabetes compared to 3.5% of those with a normal weight.

Diabetes is the "tip of the Iceberg" and is most often preceded by a metabolic syndrome. The prevalence of the metabolic syndrome gives an estimate of the potential magnitude of the problem. The Centers of Disease Control and Prevention recently investigated the prevalence of the metabolic syndrome: The unadjusted and age-adjusted prevalences were 21.8% and 23.7%, respectively. The prevalence increased from 6.7% among participants aged 20 through 29 years to 43.5% and 42.0% for participants aged 60 through 69 years and aged at least 70 years, respectively. Using 2000 census data, about 47 million US residents have the metabolic syndrome.

Most patients who go through the evolution of metabolic syndrome to diabetes will ultimately require insulin injections to deal with their disease. According to research, the well educated Type I diabetes patient encounters on average about 5 hypoglycaemic episodes and about the same hyperglycaemic episodes every week. Both conditions may lead to a variety of complications, such as lack in concentration, loss of conscience, coma, dehydration and death.

A major draw back of the algorithms used to predict glucose levels in the prior art is that the algorithms use theoretical absorption curves of the injected insulin. These curves try to predict the appearance of insulin in the bloodstream and the insulin activity which is then used in the prediction model. The current prediction algorithms do not take into account other insulin-interfering factors, and are therefore often highly inaccurate.

SUMMARY OF THE INVENTION

The present invention provides a comprehensive approach to the management of diabetes. The method of the present invention utilizes dual parameters in understanding metabolic changes in the body. A first parameter that may be utilized in accordance with the present invention may comprise biochemical signals indicative of fat metabolism (e.g., Ketones or Free Fatty Acids or Glycerol levels) and a second parameter may comprise biochemical signals indicative of glucose metabolism (e.g., glucose levels). Furthermore, the dual analyte model allows monitoring of the progression of those disease states, as well as progress made by therapeutic interventions. For insulin dependent diabetes in particular, the dual analyte model can help in the dosing of medication (insulin and others) and of dietary changes.

The measurable signals may also be used to assess a real insulin activity (the combined effect of insulin concentration, insulin sensitivity and counter-regulating hormones), to detect a discrepancy, known as an insulin activity error, between the theoretical insulin activity and the real insulin activity. The calculated insulin activity error allows for detection of currently unknown insulin over-activity, which usually leads to hypoglycaemia in the near term or to detect unknown insulin under-activity that may lead to hyperglycemia. In Type I diabetes in particular, the invention can be used to alert for upcoming glucose deregulation as well as retrospectively detect abnormal regulation episodes. Through detection of upcoming events, the dual-analyte system may advise a patient to take an action, for example, to increase testing frequency or comment on the dosing of the medication.

Through the invention, free fatty acid (FFA) levels in Type I diabetes may be used for better diabetes regulation. For example, fat metabolite levels can be used to assess the insulin activity of a patient at a given moment. A patient may be urged to test glucose levels earlier, for example, in an hour (instead of four hours, when he takes his next meal), to help identify an anticipated problem. The present invention employs body fat metabolite levels to assess actual and real insulin activity, defined as an intergration of blood insulin levels, plus insulin sensitivity, plus the activity of the counter-regulating hormones. Advice to a patient can take the form of a glucose prediction for a future period and/or recommending upon the timing of the next test.

The present invention provides a single device for testing both a fat metabolism analyte and a glucose metabolism analyte, as well as for interpreting the combined results of the dual analyte measurements.

According to a first aspect of the invention, a method of assessing an insulin activity error and its effect on glucose levels is provided. The method comprising the computer implemented steps of measuring an amount of a first analyte in a biological fluid sample reflecting body fat metabolism and an amount of a second analyte in the biological fluid sample reflecting glucose metabolism, assessing a real insulin activity level based on the amount of the first analyte in the biological fluid sample, comparing the real insulin activity with a theoretical amount of insulin to calculate the insulin activity error; and assessing a glucose level based on the amount of the second analyte in the biological fluid and the calculated insulin activity error According to another aspect of the invention, a method of predicting a user's glucose levels in the future is provided. The method comprises the computer implemented steps of measuring an amount of a first analyte in a biological fluid sample reflecting body fat metabolism and an amount of a second analyte in the biological fluid sample reflecting glucose metabolism, assessing a real insulin activity level in the user based on the amount of the first analyte and the second analyte in the biological fluid sample, comparing the real insulin activity level with a theoretical amount of insulin to calculate an insulin activity error, utilizing an additional parameter comprising at least one of: body mass index, gender, meal intake, medication, exercise duration and intensity, alcohol consumption and weight and utilizing a relevant algorithm corrected for the insulin activity error to model the glucose levels for a future period.

According to still another aspect of the invention, a health-monitoring device is provided. The health monitoring device comprises a test element and a processor. The test element measures an amount of a first analyte in a biological fluid sample reflecting body fat metabolism and an amount of a second analyte in the biological fluid sample reflecting glucose metabolism. The processor assesses a real insulin activity level of the user based on the amount of the first analyte in the biological fluid sample, compares the calculated real insulin activity with a theoretical amount of insulin to calculate an insulin activity error, and assesses a glucose level based on the amount of the second analyte in the biological fluid and the calculated insulin activity error.

BRIEF DESCRIPTION OF THE DRAWINGS

FIG. 3a is a schematic of a health monitoring system including the health monitoring device of FIGS. 1a and 1b.

FIG. 3b is a block diagram showing the components of the processor of FIG. 3a.

FIG. 8b illustrates the theoretical insulin activity with the calculated real insulin activity in the same patient as in 8a.

FIG. 9 shows the display of the device of FIG. 6 according to an embodiment when the device is used to track an intra-day evolution of glucose levels and the insulin activity error and display a warning about imminent hypoglycemia.

FIG. 10 shows the display of the device of FIG. 6 according to one embodiment of the invention, when the device is used to graphically display glucose levels and an insulin activity error.

FIG. 13B is a graph showing a glucose prediction error, an insulin activity error, incidents of unexpected hypoglycaemia and incidents of expected hypoglycaemia for the patient during the second experiment.

FIG. 15B is a graph showing a glucose prediction error, an insulin activity error, incidents of unexpected hypoglycaemia and incidents of expected hypoglycaemia for the patient during the fourth experiment.

FIG. 16B is a graph showing a glucose prediction error, an insulin activity error, incidents of unexpected hypoglycaemia and incidents of expected hypoglycaemia for the patient during the fifth experiment.

DETAILED DESCRIPTION OF THE INVENTION

Figure 1A:
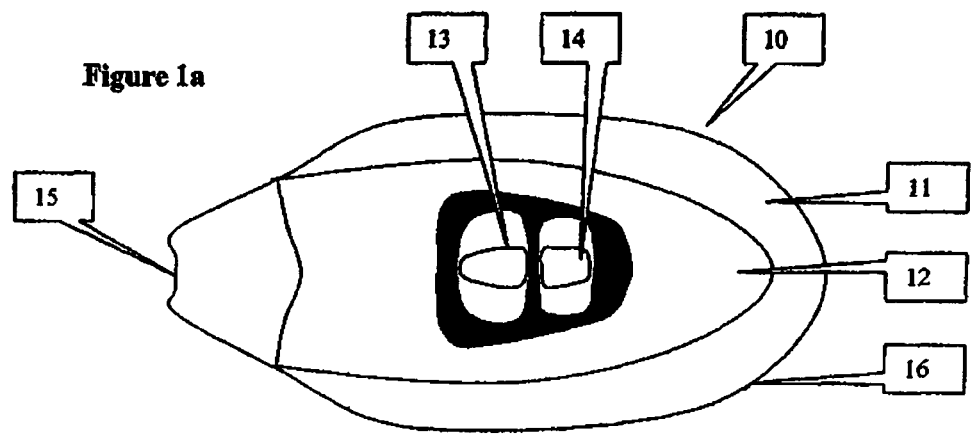
FIGS. 1a and 1b illustrate an electronic health monitoring device for sampling and analyzing a biological fluid sample and assessing the health of a user based on levels of two analytes in the sample.

The present invention provides a system and method for managing diabetes and metabolic syndrome. The system and method of the present invention tracks dual parameters and utilizes the dual parameters to understand metabolic changes, understand the real insulin activity in a user, and provide management or therapeutic advice to a user. The invention will be described below relative to illustrative embodiments.

Those skilled in the art will appreciate that the present invention may be implemented in a number of different applications and embodiments and is not specifically limited in its application to the particular embodiments depicted herein.

As used herein, the terms "fat analyte" and "fat metabolism analyte" refer to an analyte generated in a patient when consuming body fat for energy supply. Fat analytes and fat metabolism analytes include, but are not limited to, ketones, glycerol, Free Fatty Acids (FFA) and a fatty acid that is representative of the total FFA's in the system, such as Palmitate. Free Fatty Acids are a family of different fatty acids, and traditional test systems for Free Fatty Acids measure the most representative fatty acid of the family, which is usually Palmitate. However, one skilled in the art will recognize that other fatty acids present in other proportions are also representative of a total FFA level and may also be used.

As used herein, the terms "glucose analyte" and "glucose metabolism analyte" refer to an analyte indicative of glucose metabolism. Metabolic analytes indicative of glucose metabolism include, but are not limited to, glucose levels, pyruvate, glucose6phosphate and lactate.

The term "biological fluid" as used herein refers to a fluid containing a metabolic analyte, including, but not limited to blood, derivatives of bloods, interstitial fluid, urine, a breath sample, saliva, and combinations thereof.

As used herein, the term "insulin" or "medication" is intended to include any substance taken to interfere with the insulin-like activity, insulin resistance, lypolisis, insulin secretion, insulin sensitizers, Thiazolidines (TZD's). Examples include, but are not limited to, Insulin, Pioglitazone, Metformin, Glucophage and others known in the art.

As used herein, the terms "real insulin activity", "real insulin activity level" and RIA refer the actual net insulin effect on glucose and fat metabolism, i.e., the actual combined effect of insulin concentration, insulin sensitivity and counter-regulating hormones in a patient or other user.

As used herein the term "theoretical insulin level" refers to an estimated insulin level in a user based on calculations using a modeling algorithm.

As used herein, the term "insulin activity error", or IAE, refers to a discrepancy between a theoretical insulin level and a real insulin activity level found in the patient or other user.

As used herein, the term "glucose prediction error", or GPE, refers to a discrepancy between measured glucose levels and theoretical glucose levels, estimated using a modeling algorithm.

FIGS. 1a, 1b, 2, 3a, and 3b, illustrate a health-monitoring device or monitor 10 for monitoring the health of a patient according to an illustrative embodiment of the invention. The illustrative health-monitoring device 10 includes a sampling device for sampling a biological fluid, such as blood, and a testing device for measuring the levels of two analytes in the sample, for example a fat analyte and a glucose analyte, through means known in the art. The device 10 includes a processor 90, which is shown in FIGS. 3a and 3b, for running a program that uses the measured analyte levels to assess the health of a user.

Figure 2:
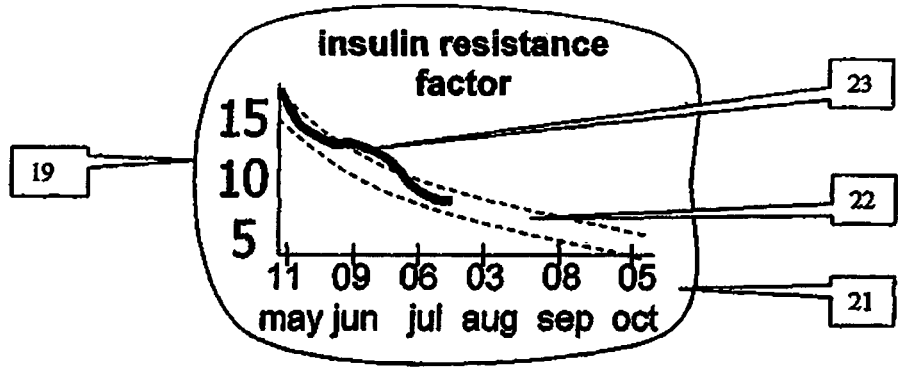
FIG. 2 illustrates the output and user interface of the device of FIGS. 1a and 1b when tracking an insulin resistance factor.

In one embodiment, the device 10 correlates fat analyte and glucose analyte measurements to a health parameter to give the user an assessment of his health. The health-monitoring device includes a display 19 for displaying results to the user, as well for providing the different options in tracking results and reading the advice. For example, as shown in FIG. 2, the illustrative device 10 calculates an insulin sensitivity factor based on the measured levels of two analytes in a user. As shown, the health-monitoring device 10 tracks the progress of the user's insulin sensitivity factor over time to provide feedback to the user regarding his health.

According to the illustrative embodiment, the health monitoring device 10 measures a fat analyte, which is indicative of fat metabolism in the user, and a glucose analyte, which is indicative of glucose metabolism in the biological fluid sample and uses the two measurements to calculate a health parameter. The fat analyte may comprise free fatty acids (FFA), ketones, glycerol or any other analyte that is indicative of lipolysis (fat breakdown) in the body.

Figure 4:
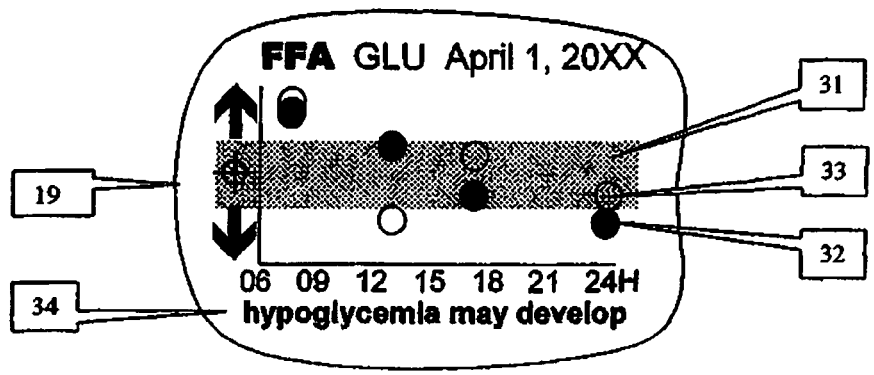
FIG. 4 shows the display of the device of FIGS. 1a and 1b when the device is used to track an intra-day evolution of glucose and FFA levels and display a warning about imminent hypoglycemia, according to an embodiment of the invention.
Figure 5:
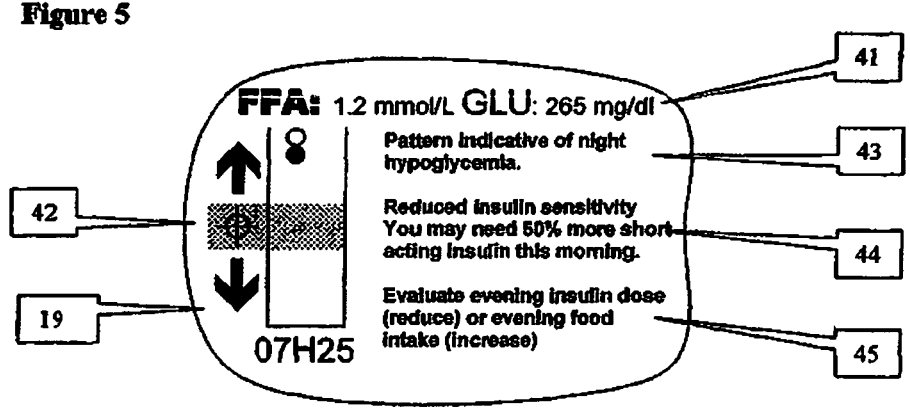
FIG. 5 shows the display of the device of FIGS. 1a and 1b when the device is used to display early morning test results for glucose and FFA and the interpretation thereof, according to an embodiment of the invention.

According to another embodiment of the invention, the device 10 may used to track an intra-day evolution of glucose and FFA levels and display a warning about imminent hypoglycemia, according to an embodiment of the invention, as shown in FIG. 4. The device 10 may also be used to display early morning test results for glucose and FFA and the interpretation thereof, as shown in FIG. 5.

Figure 6:
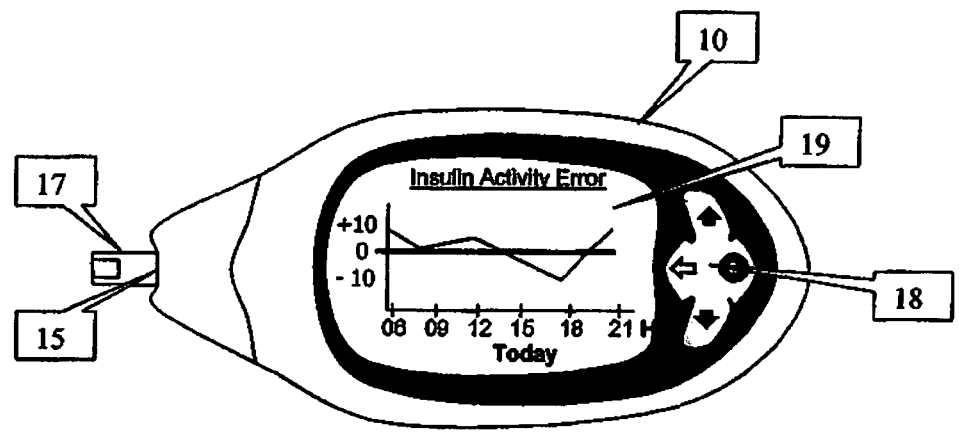
FIG. 6 illustrates an electronic monitoring device for sampling and analyzing a biological fluid sample and assessing the insulin activity error of a user based on levels of two analytes in the sample according to one embodiment of the invention.

According to another embodiment of the invention, as shown in FIGS. 6-10, the processor in the device 10 runs a program that uses the analyte levels in a sampled biological fluid to assess a real insulin activity level of the user. As shown in FIG. 6 the health monitoring device 10 of an illustrative embodiment of the invention may analyze a biological fluid sample and assesses an insulin activity error of a user over the course of a day, or other suitable time period, based on levels of two analytes in the sample. Insulin activity error refers to a discrepancy between a theoretical insulin level and a real insulin activity level found in the patient. The device of the illustrative embodiment of the invention compares the real insulin activity level with an assumed theoretical insulin activity to give the user an assessment of prospective effects on his glucose levels.

Figure 7A:
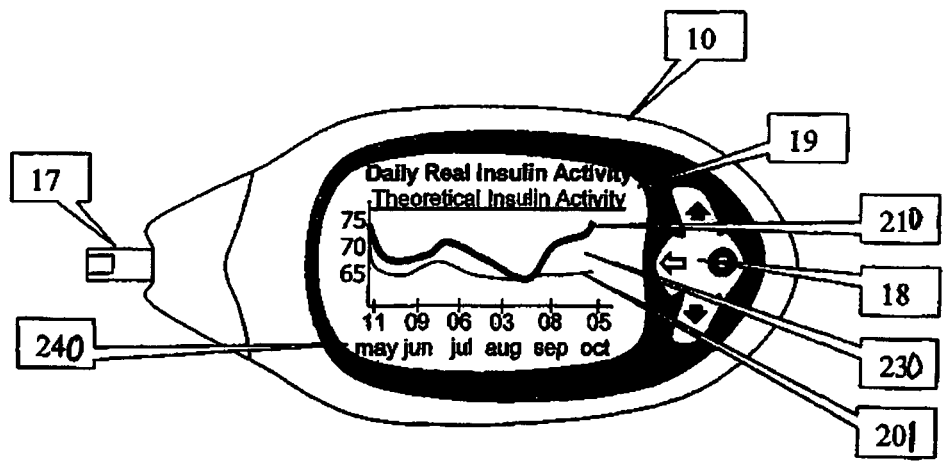
FIG. 7a illustrates the output and user interface of the device of FIG. 6 when tracking the real insulin activity of a user.
Figure 7B:
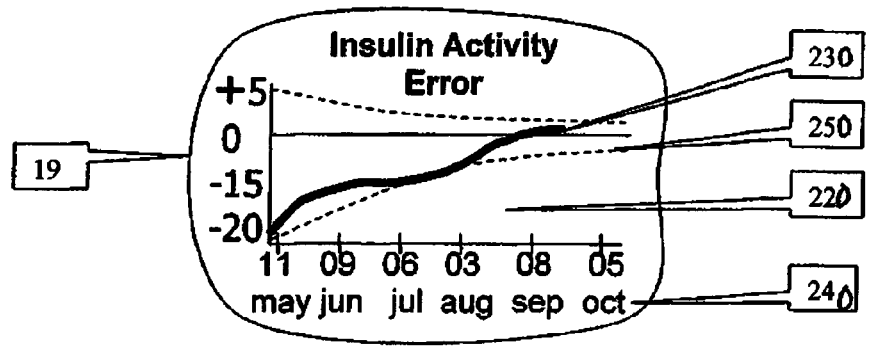
FIG. 7b shows the evolution of the insulin activity error in a user over time according to an embodiment of the invention.

In another embodiment of the invention, the device 10 may measure a user's real insulin activity levels, and compare the measured levels with theoretical insulin activity levels. For example, as shown in FIG. 7a, the display 19 may track and show the difference between a theoretical insulin activity 201 and a real insulin activity level 210 over a period of time, indicated by axis 240. The difference is graphically represented as an insulin activity error 230, which may also be tracked. As shown in FIG. 7b, the insulin activity error 230 may be tracked over a period of time, such as over several months, as shown. A positive error indicates more insulin activity than assumed from the theoretical insulin absorption curves.

Based on the assessment, the device 10 may automatically calculate and provide advice to a patient. For example, the device may formulate test frequency advice to the user based on measurements of the two analyte levels. The device 10 may formulate insulin dosing or other medication dosing advice to the user, or automatically instruct the right insulin dose to an insulin delivery device employed by the user.

Referring back to FIG. 1, the device 10 includes a housing 11, which incorporates a sampling device, illustrated as a lancing device 12 having a lancet, for piercing the skin of a user. The sampling device is used to yield a biological fluid sample containing one or more of the analytes to be measured. The lancing device 12 may include a variable depth selector 14 for setting the penetration depth of the lancet and a trigger button 13 for releasing the lancet to prick the skin. One skilled in the art will appreciate that the lancing device does not have to be incorporated into the health-monitoring device 10 but can be a separate stand alone device. Alternatively to the lancet, a hollow needle may be used to extract the sample from or from within the skin. The sampling device may comprise any suitable means for yielding a biological fluid sample and is not limited to a lancing device or other device for piercing the skin of a user.

The illustrative testing device 10 includes a test port 15, which allows a disposable test element 17 to be inserted into the apparatus. The test element 17 may comprises any suitable device for measuring analytes, including, but not limited to a test strip, a skin inserted device, such as a catheter, or a measuring device that uses a non-invasive methods of measurement which may not utilize a body fluid sample. The test element 17 generates a signal indicative of the concentration of the tested metabolic analytes in the sample, which can be based either on a photometric, electrochemical analytical method or any other suitable method known in the art. The test port 15 may include electrical contacts for reading the signal of an electrochemical based test strip or may hold a photometric or reflectometric cell to read the signal of a photometric test strip. Other readers can be used in accordance with the teachings of the invention, including, but not limited to a fluorescence reader, magnetic reader, and others known to those of ordinary skill in the art, depending on the utilized test element or assay technology.

One single test element 17 may be utilized to measure both analytes, so that the patient has to sample only once (i.e. stick his finger to obtain a blood drop) to obtain both results. Alternatively, a different test element can be used for each analyte measured in the patient. For example, one analyte can be measured by one method (i.e., photometrically), and the other by another method (i.e., electrochemically), and the meter may incorporate both methods.

Based on the measured levels of the analytes in the biological sample, a processor in the health-monitoring device 10 calculates a health parameter, such as a real insulin activity level, a prospective glucose level, and/or an insulin activity error, and provides feedback to the user regarding the calculated health parameter.

A data communication port 16 in the housing 11 allows insertion of an electrical connector to access the electronics in the device 10. This feature can be used to download, as well as upload, data and programs. One skilled in the art will recognize that communication between the electronics is not limited to electrical communication. Acoustic, optic (infrared), radio waves or other communication means known in the art may be used as well.

The illustrative device 10 may include an interface button 18 for navigating menu options presented on the display 19 or to select and confirm data inputs and outputs.

Figure 1B:
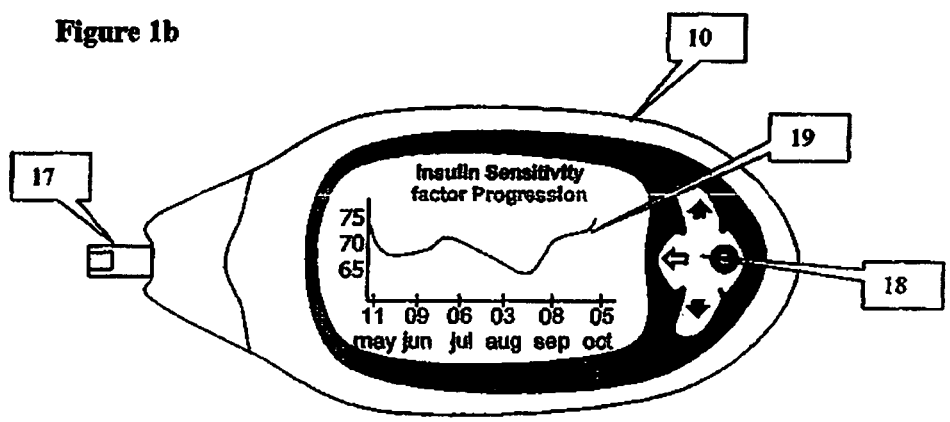

The correlation between the measured analyte levels and the health of a user, assessed using a program stored in the device 10 of FIGS. 1a and 1b, the real insulin activity, and/or an insulin activity error assessed using a program stored in the device 10 of FIG. 6, will be described in greater detail below.

The illustrated monitor 1 0 contains electronics, including a processor 90 for reading and receiving a signal from the test element 17, shown in FIG. 3a and 3b. By using the calibration information for the test element, the processor 90 can convert the measured signals generated by the test element 17 to a concentration of each of the tested metabolic analytes. The processor 90 provides feedback to a user based on the levels of the first and second metabolic analyte in a biological fluid sample. The processor 90 includes a calculator 92 for determining the level of the first metabolic analyte, such as a fat analyte, and a second metabolic analyte, such as a glucose analyte in the sample. The processor 90 also includes a correlator 94 for correlating the levels of the first and second metabolic analyte to a health parameter indicative of the user's health. Alternatively, the correlator 94 may correlate the levels of the first and second metabolic analytes to the real insulin activity in a user, and calculate an insulin activity error representing a discrepancy between the real insulin activity and a theoretical insulin activity level. The measured analyte concentration can be displayed on the display 19 and/or stored into memory of the monitor 10.

In one embodiment, as shown in FIG. 3a, the monitor 10 may form part of a health monitoring system 300. The health monitoring system comprises the monitor 10 and a remote site 72 having a database 74 for storing data obtained by the monitor 10. As shown, the monitor may be connected to the remote site 72 over a network 76.

According to an illustrative embodiment of the invention, the health monitoring device 10 utilizes and implements relationships between fat analytes and glucose analytes in the body and parameters indicative of the health of a user. The processor 90 may be programmed to calculate a health parameter based on known relationships between levels of fat analytes and glucose analytes and certain health parameters. For example, in the human body, levels of free fatty acids (FFA) rise when there is a rise in insulin action and a raise in counter-regulating hormones. Obesity is also commonly associated with elevated plasma free fatty acid (FFA) levels, as well as with insulin resistance and hyperinsulinemia, two important cardiovascular risk factors.

Free Fatty Acids and Lipid Metabolism

A drop in insulin action and a rise in counter-regulating hormones also tends to cause a rise in Free Fatty Acids (FFA) in the human body. Adipose tissue plays an important role in energy supply. In the absence of sufficient glucose to meet the body's energy needs, lipolysis, i.e., fat breakdown, supplies Free Fatty Acids for energy. Body fat is broken down to release Free Fatty Acids (FFA) and glycerol into the circulation. This typically occurs in the post-absorptive phase (the time span between the digestion of a meal and the start of the next meal) and overnight (the longest fasting period of the day). The regulation of lipolysis is under control of a variety of hormones, including insulin, glucagon, growth hormone (GH), epinephrine, adrenalin and cortisol.

Under caloric restriction, glucose levels in the body drop progressively, and then stabilize. As a reaction, plasma levels of insulin drop while glucagon levels increase. The result of this decreased insulin/glucagon ratio is a lipolytic effect on the fat tissue, which releases FFA into the blood stream. The FFA generally have two destinations: some are consumed directly by the body tissues for energy, other enter the liver cells for ketogenesis (beta-oxidation to form ketones). In addition, glucagon will also stimulate the liberation of glucose from the liver and muscle stores to compensate for a shortage of glucose.

Besides glucagon, other hormones will try to compensate for the shortage of glucose. Growth hormone, for example, plays an important role during the night to ensure sufficient energy substrates are available. Growth hormone (GH) infusion in normal subjects increases glycerol and FFA concentrations, indicating an enhanced lipolysis. The ketogenetic effect of growth hormone is explained by the increase of substrate (FFA) through enhanced lipolysis. Growth hormone secretion is typically increased early in the night to compensate for dropping glucose levels in the blood. Dropping glucose concentration and insulin levels triggers the increase in GH secretion. In insulin dependent diabetes, GH secretion is markedly increased, especially in adolescents and patients with poorly controlled diabetes.

It has been suggested that there is a negative feedback loop between FFA and Growth Hormone. Lack of FFA itself may be the signal for growth hormone release despite the lag (generally about 2 hours) period between FFA decrease and Growth hormone increase. Glucose and FFA can not fully replace each other in their respective influence on growth hormone.

GH effects during the night may play an important role to the origin of the "dawn-phenomenon" found in diabetic patients, a low glucose level during the night followed by a high glucose at wake with an increased need for insulin. The typical increase of FFA, most often a doubling of the baseline levels, generally occurs between 2 and 3 hours after the GH peak.

Adrenaline and epinephrine, two hormones produced under stress conditions also stimulate lipolysis in an attempt to ensure sufficient energy substrates.

In summary, FFA rises due to a drop in insulin action and a raise in counter-regulating hormones. The raise in counter-regulating hormones is influenced by a couple triggers, which can sometimes be unpredictable, such as meal intake during the day and GH, stress and nervosa for adrenalin and epinephrine, the circulating level of insulin and the glucose concentration in the blood. Therefore, the rise in FFA's and their association with insulin sensitivity and glucose levels is unpredictable and justifies the need for frequent monitoring.
Lipolytic Parameters.

According to an illustrative embodiment, the monitoring devices measures and correlates Free Fatty Acid levels to analyze a user's health, though one skilled in the art will recognize that any analyte that reflects lipolysis can be used. For example, other analytes, such as ketones and glycerol are also products from lipolysis, and can be used to assess the effect of the counter-regulating hormones in the body. As described above, under a condition of low insulin, low glucose and high counter-regulating hormones (such as, but not limited to Growth hormone, glucagon, cortisol, epinephrine and noradrenaline), lipolysis is stimulated to supply other sources of energy than glucose. Body fat is stored as triglycerides, which is a molecule made up of three free fatty acid (FFA) chains and one glycerol. Lipolysis will thus liberate FFA and glycerol from the fat stores into the circulation. The FFA's can enter body cells (but not neural tissue cells), and be oxidized. FFA can also enter the liver mitochondria and be converted to ketones, also a source of energy but in high concentration those can be toxic. Glycerol will contribute to the new formation of glucose.

FIG. 2 illustrates the use of the health-monitoring device 10 to monitor a successful therapeutic effect over the course of months. As shown, the display 19 of the device 10 may be used to display a graph 21, which tracks a user's insulin resistance factor by graphing a curve 23 over time. The graph may also display a therapeutic goal 22 (graphed as a zone) which was set for the particular patient. The device 10 may compare the user's actual insulin resistance factor with a set goal to provide feedback and motivation to the user.

The device 10 may also be used to monitor insulin dependent diabetes patients. Insulin dependent diabetes patients are characterized, among other elements, by a shortage or even absence of insulin. Typically, these patients are treated through self-administration of insulin. Insulin, which is injected by the patient himself, comes in different forms: some preparations have a very fast and short action profile and are used typically to clear the carbohydrates from the blood stream after a meal. Other preparations have a long half-life time and are used to supply a patient with a more or less stable base amount of insulin throughout the day and night.

It is the duty of the patient to balance the amount of these two insulin types with the size and composition of his meals, exercise, stress levels, sickness, and sleep and wake cycles. The goal of such a treatment is to achieve near-normal glucose levels. Some patients may use an insulin pump, which delivers continuously a self-selected amount of insulin through a catheter. Self-management is daunting task for the average person with diabetes.

A major challenge in the management of insulin dependent diabetes is to endure the night (the longest period of fasting) with close to normal glucose levels while avoiding hypoglycemia. The lack of food intake over this period makes it difficult not to overdose insulin whilst avoiding hyperglycemia. An additional problem facing insulin dependent diabetics is the long period that needs to be covered without an intervention, such as a glucose test, a meal or insulin injection (since the patient is asleep). Hypoglycemia at night is complicated by the absence of external notice of the problem and of external intervention.

Glucose levels tend to fall in the first half of the night as the evening meal is digested and the glucose absorbed into the muscle and liver. The counter-regulating hormones, especially Growth hormone and glucagon, start to stimulate lipolysis to supply the body with FFAs and glycerol as energetic substrates for metabolism. The substitution of Glucose by FFAs for the energy needs saves the further consumption of glucose by muscle and other tissues, freeing up glucose for oxidation by the neural tissues (brain, nerves) to maintain metabolism. Glycerol will contribute to the neogenesis of glucose. Those two elements will cause the glucose level to increase by early morning. Cortisol levels increase as well before waken up and have a similar hyperglycemic effect.

As a result, night hypoglycemia may not be recognized in the early morning glucose values. However the FFA levels before breakfast may give insight in the level of lipolysis occurring overnight, reflecting the degree of hypoglycemia of the previous night period.

Depending on the relative imbalance between the evening and/or bedtime food intake and the amount of injected insulin, glucose levels in the morning can vary substantially.

Thus, high glucose levels in the morning may result from a relative overdose of insulin the evening before. High FFA levels at wake indicate a hypoglycemia overnight. When coinciding with high glucose levels, this condition should not be treated with a higher insulin dose at bedtime.

A milder form of the counter-regulating hormone action is known as the "dawn-phenomenon", a condition that occurs when a patient wakes up with a high glucose level and high ketone levels (indicative for the enhanced lipolysis) as a reaction to low overnight glucose levels. Insulin dependent patients tend to require more insulin in the morning to lower their blood glucose than during the course of the day. This reduced insulin sensitivity, caused by the counter-regulating hormones (even in absence of night hypoglycemia) may be assessed by measuring FFA levels together with the glucose level in the morning before breakfast. FFA levels can double at wake in the existence of the Dawn-phenomenon.

The health-monitoring device 10 may also be used to provide assistance in determining insulin dosage, based upon both the glucose levels and the FFA levels in the user. For example, the health-monitoring device 10 may be used to retrospectively assess night hypoglycemia utilizing measured FFA levels. As described, glucose levels alone are not ideal to dose insulin. Glucose readings can be normal to very high in the morning as a consequence of hypoglycemia overnight. This situation is rather caused by an over-dosing of insulin relative to the meal intake in the evening. These patients with high glucose and high FFA in the morning should reduce insulin (or increase caloric intake or change meal composition) in the evening rather than take more insulin, which is the natural reflex. Current practice in self-dosing of insulin lacks the counter-regulating hormone information and works with glucose levels alone. Most often this results in patients taking more insulin the next evening to tackle the hyperglycemia. As a consequence, the following night even more severe hypolycemia and consequential hyperglycemia can be the result. It usually takes several days to get back into control.

For example, FIG. 5 shows the display 19 of the health-monitoring device 10 of FIG. 1 according to one embodiment when the device is used to display early morning test results for the two analytes. As shown, the display 19 of FIG. 5 displays a first analyte measurement, illustrated as the free fatty acid measurement and a second analyte measurement, illustrated as the glucose measurement, in measurement region 41. The device compares the measurements to the target range, shown in target region 42. The illustrative device 10 may identify the analyte pattern typical for night hypoglycemia and may provide a diagnosis to the user, shown in diagnosis region 43 of the display 19. For example, as shown, the device 10 may conclude that the patient should reduce his evening insulin to avoid repetition of a night hypoglycemia, as show by the recommendation 45. In addition, as a consequence of the high FFA in the morning, the device may calculate and inform the patient that, for example, 50% more insulin will be needed to tackle the increased insulin resistance, as shown in dosage region 44 of the display 19.

The health monitoring device may also be used to identify over-insulinized patients by measuring FFA levels. The risk exists that the patient becomes trapped in a cycle of increasing his insulin each time he perceives a high glucose reading. Ignorant about the effects of the counter-regulating hormones, a patient may end up with frequent high levels of both FFA and glucose, and a low insulin sensitivity while consuming large amounts of insulin. The medical community has started to recognize this logical self-perpetuating cycle. The only efficient, though intuitively contrary approach is to drastically reduce the insulin intake to restore the hypoglycemia, reduce the FFA levels and improve the insulin sensitivity. Therefore, information regarding FFA combined with glucose levels, as measured and analyzed using the device 10, may provide information early to the patient so he can avoid over-insulinization or restore insulin sensitivity.

As shown in FIG. 1, the device 10 of the present invention may be used to track the evolution of an insulin sensitivity factor in a patient. Depending on the volatility of the insulin sensitivity factor and the therapeutic goals, the time basis for the tracking can be changed, showing the evolution over weeks or days, rather than months. An (averaged) intra-day evolution can reveal even more detailed information. Consistent low insulin sensitivity in the late afternoon, for example, may signal the patient to reduce insulin before lunch or increase the lunch calorie content or composition.

According to another embodiment of the invention, the device 10 can measure and utilize FFA and glucose levels to assess the prospective development of hypoglycemia and hyperglycemia in a patient. For example, FIG. 4 shows use of the device 10 of the illustrative embodiment of the present invention to inform the user regarding potential imminent hypoglycemia, as shown in FIG. 4. The challenge of the night hypoglycemia and "dawn phenomenon" treatment is to avoid low glucose levels overnight primarily by identifying the conditions in advance. FFA levels in combination with glucose measurements, as detected by the device 10, can help to avoid low glucose levels overnight. Certain patterns, such as a normal to low glucose level in the presence of low FFA level at bedtime or early night, may indicate the development of hypoglycemia in the near future. By detecting this pattern, the system and method of the invention may help the patient to take preventive steps to avoid imminent hypoglycemia. The device may provide recommendations to the patient, such as to take an extra snack (with slow absorbing carbohydrates) before going to sleep. As shown in FIG. 4, the device 10 graphs both free fatty acid levels 32 and glucose levels 33 on the display 19 and compares the measured levels to a therapeutic goal, illustrated as region 31. The display may display a message 34 that warns the user of potential hypoglycemia, based on the measured analytes. In FIG. 4, the illustrative device 10 recognizes that although the glucose reading 31 is near normal, the low FFA level 32 indicates a strong insulin activity in spite of the already normal to low glucose level.

In the opposite case, when the glucose level is normal to high in the presence of a high FFA level at bedtime or early night, one might expect a hyperglycemic response. This situation typically occurs when insufficient insulin is available. The high FFA level in combination with the lack of insulin action may result in keto-acidosis, which can be a life threatening condition and may lead to a coma. When such a condition exists, the device 10 can detect the condition and may recommend to the patient to take extra insulin or reduce food intake to correct the condition.

The Correlation of the Analyte Levels to the Real Insulin Activity in a User:

FIGS. 6-10 relate to use of a health monitoring device of an illustrative embodiment of the invention for the correlation of the analyte levels to a real insulin activity level and for providing a measurement indicative of a difference (i.e., insulin activity error) between real insulin levels and theoretical insulin levels according to another embodiment of the invention. Particular challenges are inherent to regulate glucose levels in Type I diabetes. Type I patients lack the required insulin production (partially or completely). Such a patient is required to dose his insulin accurately and inject himself several times a day. The dosing of the insulin is based on the diabetic patient's assumed food intake, his basic metabolic rate, sleep and wake cycle, exercise sessions, episodes of sickness, emotional stress, and other factors.

Current algorithms for dosing insulin are based on a theoretical absorption (appearance in the bloodstream) of the subcutaneous injected insulin dose and are inadequate. To help absorb the carbohydrates and fats from a meal, the patient injects himself with a quantity of short-acting insulin prior to each meal. The insulin needed for the basal metabolism is covered by a once-a-day injection of long-acting insulin. In the theoretical patient, these interventions keep his blood glucose levels within physiological limits. However, a series of unpredictable interferences interact with the insulin absorption and its activity, resulting in hypo- and hyper-glycaemic episodes as well as unwanted counter-regulating events.

Therefore, a real insulin activity level in a user is often different from the theoretical level, leading to an inability to accurately control one's health.

This embodiment of the invention facilitates assessment of the discrepancy between the "real insulin activity" and the "theoretical insulin activity" to provide a parameter known as an "insulin activity error", which may then be used to control the patient's insulin more accurately and promote the patient's overall health.

The Real Insulin Activity:

The illustrative embodiments of the invention define real insulin activity as the net insulin effect on glucose and fat metabolism. Different components contribute to this real insulin activity and its difference with the theoretical insulin activity, including the variability in the absorption of insulin, the presence of counter-regulating hormones, the presence of anti-insulin antibodies, the clearance of insulin from the circulation, insulin sensitivity of the tissues, and other factors. The present invention may calculate and track the difference between the real insulin activity and the theoretical insulin activity in a user to promote the overall health of the user.

For the factor of variability of the absorption, there is a great variance in absorption of subcutaneously injected insulin. Using the plasma concentration of insulin eliminates the variance in absorption of the subcutaneously injected insulin. This variability can be significant depending on, the site of injection, the nature of the injection site, and the depth of the injection. For example, there is a difference in absorption between injections to the belly, which tend to be fast absorbing, and to the leg, which tend to be slow absorbing. In addition, injecting in the same (scarred) skin areas gives a slower absorption. Blood flow and vasodilatation around the injected bolus also varies with emotion, stress and temperature. In addition, insulin injected into the muscle (too deep) will appear faster in the bloodstream than the correct subcutaneous injection. Therefore, these and other factors affect how quickly the insulin is absorbed, which in turn may cause a discrepancy between a real insulin activity level and an expected or theoretical insulin activity level.

A series of hormones present in plasma, known as counter-regulating hormones, exert the opposite effect on glucose and fat metabolism. For example, Growth hormone, Glucagon, Cortisol, Catecholamines and others have hyperglycaemic effects on glucose metabolism. They elevate glucose levels through the release of glucose from the glycogen stores in the liver, the supply of an alternative energy source (FFA from fat depots) and inhibit the storage of glucose. Some of these hormones actions explain typical deregulation in Type I diabetes: Stress (catecholamines and cortisol) coincides often with high glucose levels. In addition, counter-regulating hormones have a particular action on fat metabolism: Lipolysis, or the release of Free Fatty Acids (FFA) into the circulation for energy supply. Therefore, the presence or absence of such hormones may cause a discrepancy between a real insulin activity level and an expected or theoretical insulin activity level.

A variety of different anti-insulin antibodies to insulin have been discovered. They partially or completely inactivate the insulin they bind to, also affecting the real insulin activity level and potentially causing a discrepancy between a real insulin activity level and an expected or theoretical insulin activity level.

In addition, there are individual variations in the clearance of active insulin from the bloodstream, which may affect the actual level of insulin in the blood.

The individual response to a dose of insulin is also dependent on sensitivity of the body's organs to insulin. Muscle, the main consumer organ of glucose and FFA, can have a variable response to the same dose of insulin. The sensitivity varies from person to person, in function of the severity of the disease and obesitas. The sensitivity also varies during the day. Some of the underlying causes of insulin resistance include, but are not limited to, that at the muscle level high FFA concentration inhibits glucose uptake, glycogen synthesis and glucose oxidation and that the effects will reduce the clearance of glucose from the bloodstream, resulting in high glucose levels. More insulin will therefore be needed to maintain normal glucose levels.

All current methods do not compensate for those interfering factors and rely on the appearance of insulin in plasma based on the theoretical absorption curves. The illustrative embodiment of the invention incorporates all of them by assessing the real insulin activity based on the measurement of an analyte from fat metabolism and glucose metabolism, rather than inaccurate estimations.

Assessing the Real Insulin Activity:

In addition, fat tissue metabolites reflect the real insulin activity in a patient. A drop in insulin action and a rise in counter-regulating hormones tend to cause a rise in Free Fatty Acids (FFA). Adipose tissue plays an important role in energy supply. In the absence of sufficient glucose and insulin to meet the body's energy needs, lipolysis supplies Free Fatty Acids for energy. Body fat is broken down to release Free Fatty Acids (FFA) and glycerol into the circulation. This typically occurs in the post-absorptive phase (the time span between the digestion of a meal and the start of the next meal) and overnight (the longest fasting period of the 24 H-day). The regulation of lipolysis is under control of a variety of hormones, including insulin, glucagon, growth hormone (GH), epinephrine, adrenalin and cortisol.

Figure 8A:
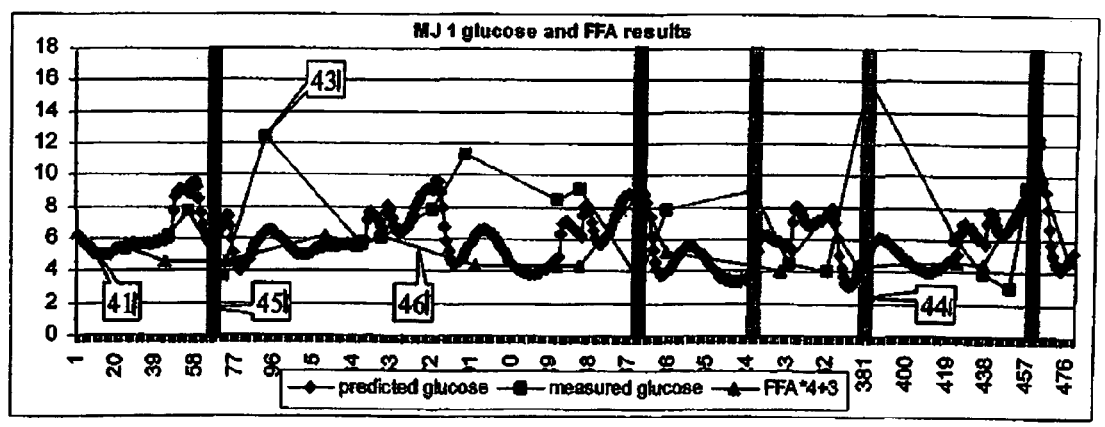
FIG. 8a displays a traditional glucose prediction curve and measured glucose and free fatty acid values of a patient over 5 days.
Figure 8B:
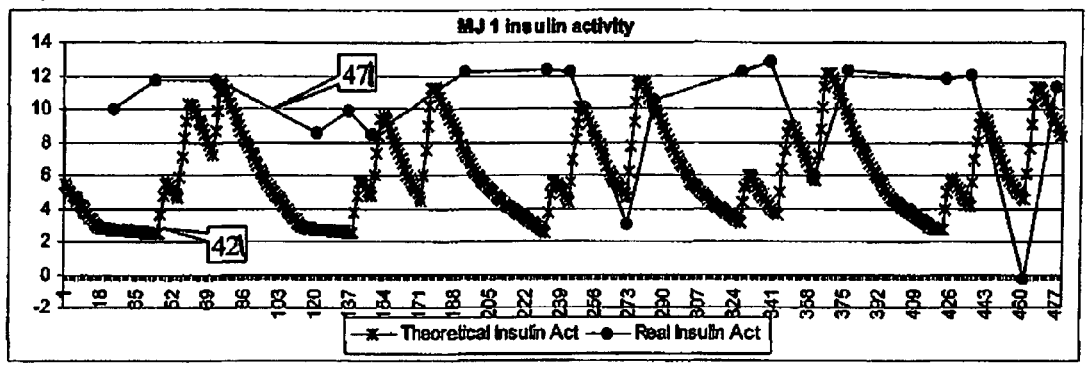
Figure 8C:
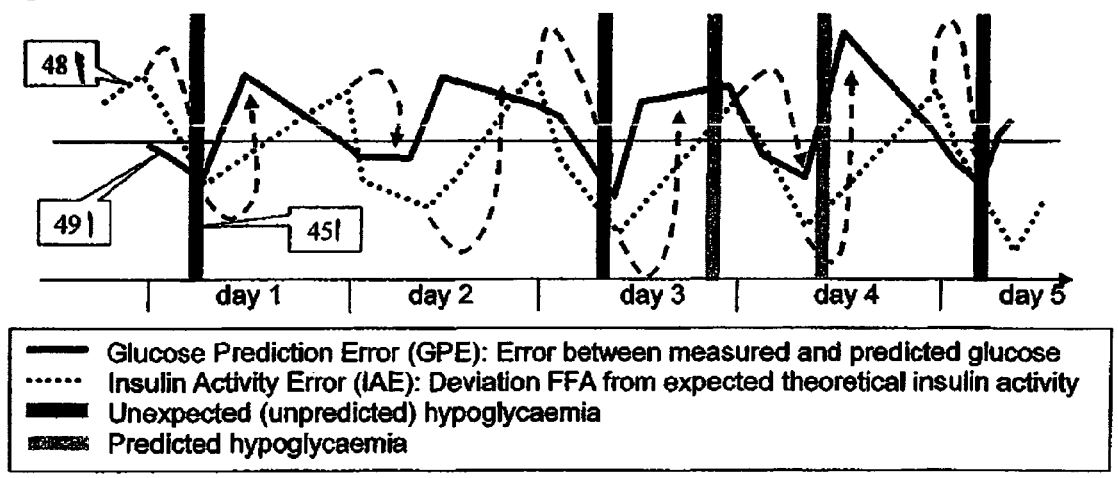
FIG. 8c illustrates the impact of the insulin activity error on the glucose prediction error in the same patient as 8a and 8b.

An illustrative embodiment of the invention uses FFA measurements to reflect the insulin, counter-regulating hormones and insulin sensitivity to compose the real insulin activity, as shown in FIGS. 8A-8C.

One or more additional parameters, such as body mass index, gender, meal intake, medication, exercise duration and intensity, alcohol consumption and weight, may be utilized in an algorithm run by the health-monitoring device 10 to correct for the insulin activity error calculated in the manner described above. The algorithm correcting for the insulin activity error may be used to model the glucose levels in the patient for a future period.

In FIG. 8A, a traditional glucose prediction algorithm (such as DIASnet) is used to predict near term glucose levels 411 in function of the injected quantity and type of insulin, the theoretical insulin absorption curves, the meal intake, the theoretical gut absorption curves, as well as the duration and intensity of exercise. The predictive accuracy is poor of such algorithms. FIG. 8A clearly shows the measured glucose values 431 deviating from the predicted glucose levels 411.

This algorithm, in the ideal predictable patient, may predict the obvious hypo- and hyper-glycaemic episodes 441 due to a known mistake such as: skipping a meal, injecting too little or too much insulin.

In the real patient, about half the hypo- or hyper-glycaemic episodes are not detected by such algorithm. FIGS. 8A and 8C show three unpredicted hypoglycaemic episodes 451 that occur in a patient, as able to be tracked by a health monitoring device of an illustrative embodiment of the invention, while only two episodes 441 were predicted according to traditional methods.

The illustrative embodiment of the invention corrects the classical glucose prediction models by measuring the FFA levels 461 and consequently correcting the theoretical insulin activity 421. FIG. 8B shows the theoretical insulin curve 421 with the real insulin activity 471, illustrating a discrepancy between the two levels, as tracked using the illustrative health monitoring device. This real insulin activity is a mathematical reciprocal conversion of the FFA levels 461. The mathematical conversion is done for scaling and range purposes. The reciprocal function is introduced because of the inverse relationship between FFA and insulin activity. The units in the Y-axis are arbitrary.

From the calculations shown in FIG. 8B, the difference between the theoretical insulin activity 421 and the real insulin activity 471 is calculated. This difference, the insulin activity error, is shown in FIG. 8C as a curve 481 and can be tracked and displayed on the display 19 of the health-monitoring device 10, as shown in FIGS. 6-7B.

As shown in FIG. 8A, the difference between the predicted glucose values 411 and the measured glucose values 431 can also be tracked using the device of the present invention. This difference, the glucose prediction error, is shown in FIG. 8C as a curve 491.

As shown in FIG. 8C, the glucose prediction error (GPE) 491 calculated according to the teachings of the invention can be either positive, when the measured glucose level is higher than predicted, or negative, when the measured glucose level is lower than predicted. A negative GPE does not necessarily leads to a hypoglycaemia incident. Rather, the occurrence of hypoglycaemia depends upon how low the absolute glucose level is in the patient.

As shown in FIG. 8C, the health monitoring device may employ the insulin activity error (IAE) 48 to explain the glucose prediction error 491. As described above, the "Insulin Activity Error" refers to the difference between a real insulin activity and a theoretical insulin activity. As shown, the unexpected hypo- and hyper-glycemic episodes 451 are anticipated by a significant IAE.

Typically, a strong positive IAE 481 (indicating a higher Real Insulin Activity than in the theoretical model) would lead within 4-6 hours to a much lower than predicted glucose level (a negative GPE) 491, and vice versa, which can be tracked, predicted and monitored using the illustrative health monitoring device.

Therefore, the calculation of an insulin activity error according to an illustrative embodiment of the invention can be useful in promoting the health of a user.

Applications of the Real Insulin Activity and the Insulin Activity Error

Referring to FIG. 9, a home monitor device 10 of an embodiment of the invention may test for both glucose and FFA's (glycerol or ketone bodies), preferably in a combined strip. Each time the patient test his pre-prandial glucose level, the device may measure the FFA (glycerol or ketones) level as well. In one embodiment, only the glucose result is displayed in area 52 of the screen 19, while the FFA testing and the FFA vs. insulin algorithm runs in the background, invisible to the patient. However, the FFA levels may also be displayed on the screen 19 in accordance with the teachings of the invention.

Upon detection of an imminent insulin under- or over-activity, the monitor may advise the patient to increase his testing frequency, as shown in area 51 on the screen 19 of the device. By doing so, the patient may pick up unexpected high or low glucose levels as they start to develop and prior to any damage to his health.

Inputs to the device to provide the results shown in FIG. 9 may include glucose and FFA levels, information regarding meals, insulin injections, exercise, and/or alcohol intake. The Glucose and FFA (glycerol or ketones) levels are preferably tested four times a day: before each meal and at bedtime. The meal information may include only the carbohydrate intake in bread units or grams, or any suitable parameter. Information regarding insulin injections may include the type and number of insulin units.

The output from the device shown in FIG. 9 is preferably advice on the testing frequency to guide a patient through a critical deregulation period. The system may or may not justify the reason of its advice: "Start testing every hour, more insulin activity is coming" or "Start testing every hour, your glucose may drop more than expected" 51.

As shown in FIG. 10, the health monitoring device may display the glucose result 52 against the therapeutic target range 53 in display 19. In addition, the insulin activity error 54 can also be graphically presented against a target range, illustrating to the user that the combination of a near-normal glucose level together with a high insulin activity error is becoming dangerous.

The use of a health monitoring device to determine glucose levels, free fatty acid levels, calculate an insulin activity error and/or provide advice to a patient, as shown in FIG. 6-10, provides significant benefits to a patient. For example, the user will be alerted in advance by both predicted and unpredicted low or high glucose levels. The advance notice is usually 4 to 8 hours, but can be any suitable time period. The user can decide to take pre-emptive measures. For example, the care taker of a child can make sure the child is put to sleep with normal glucose levels and a normal insulin activity, a patient can take an additional or a corrected amount of insulin, take more or less carbohydrates and/or can decide to take an evening snack or delete it, in response to the output from the device 10.

Alternatively, or in addition, the user can track the deteriorating glucose levels and take appropriate intervention action. For example, the user can seek medical help in time, avoid the keto-acidosis to develop by treating his hyperglycaemia, and/or treat the hypoglycaemia.

The heath-monitoring device of the present invention may also or alternatively be used to identify over-insulinization. Frequent episodes of hypoglycaemia and the rebound hyperglycemia are often due to over-insulinization. Over-insulinization is detected by finding frequent or consistent episodes of high real insulin activity or negative insulin activity errors. The patient or health care professional can adapt the insulin regime for avoiding this very frequent phenomenon.

The device may also empower patients with a low test frequency to take control. Both expected and unexpected low or high glucose levels happen probably once to twice per 24 hours and are the main reason why patients feel that they cannot manage their diabetes. Consequently they test less because they feel unable to "do it right". They usually test because "their HCP told them to test". When those patients feel low or high, they experience this as a confirmation of their inability to cope with the disease.

It is therefore likely that those patients will resume testing when their glucose system adds advanced information of what might happen in the near future so they can now take advanced precautions. The invention can empower patients testing only once or twice a day to test 4 times a day. In addition, when patients will follow the test frequency advice, they will be able to avoid a significant number of hypo- and hyper-glycaemic episodes.

The monitoring device may also be used to provide assistance in determining insulin dosage, based upon both the glucose levels and the FFA levels in the user. For example, as shown in FIG. 10, the device may identify hypoglycaemia retrospectively.

As described, glucose levels alone are not ideal to dose insulin. Glucose readings can be normal to very high in the morning as a consequence of hypoglycaemia overnight. This situation is rather caused by an over-dosing of insulin relative to the meal intake in the evening. These patients with high glucose and high FFA in the morning should reduce insulin (or increase caloric intake or change meal composition) in the evening rather than the natural reflex of taking more insulin. Current practice in self-dosing of insulin lacks the counter-regulating hormone information and works with glucose levels alone. In contrast, the present invention allows more accurate control of glucose levels.

High FFA levels in the morning may indicate a strong counter-regulating hormone activity. This translates into a low real insulin activity. The strong negative insulin activity error together with normal to high glucose level is indicative of a past hypoglycaemic episode, which may be identified using the device of the present invention.

Figure 11:
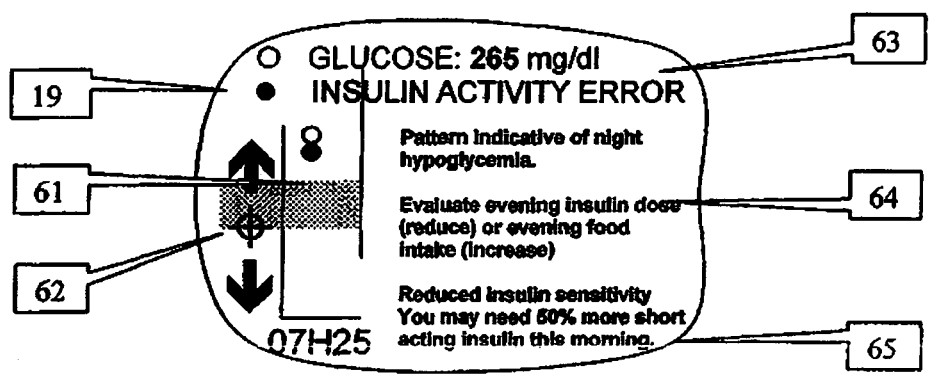
FIG. 11 shows the display of the device of FIG. 6 according to an embodiment of the invention, when the device is used to display early morning test results for glucose levels and insulin activity error and the interpretation thereof.
Figure 12A:
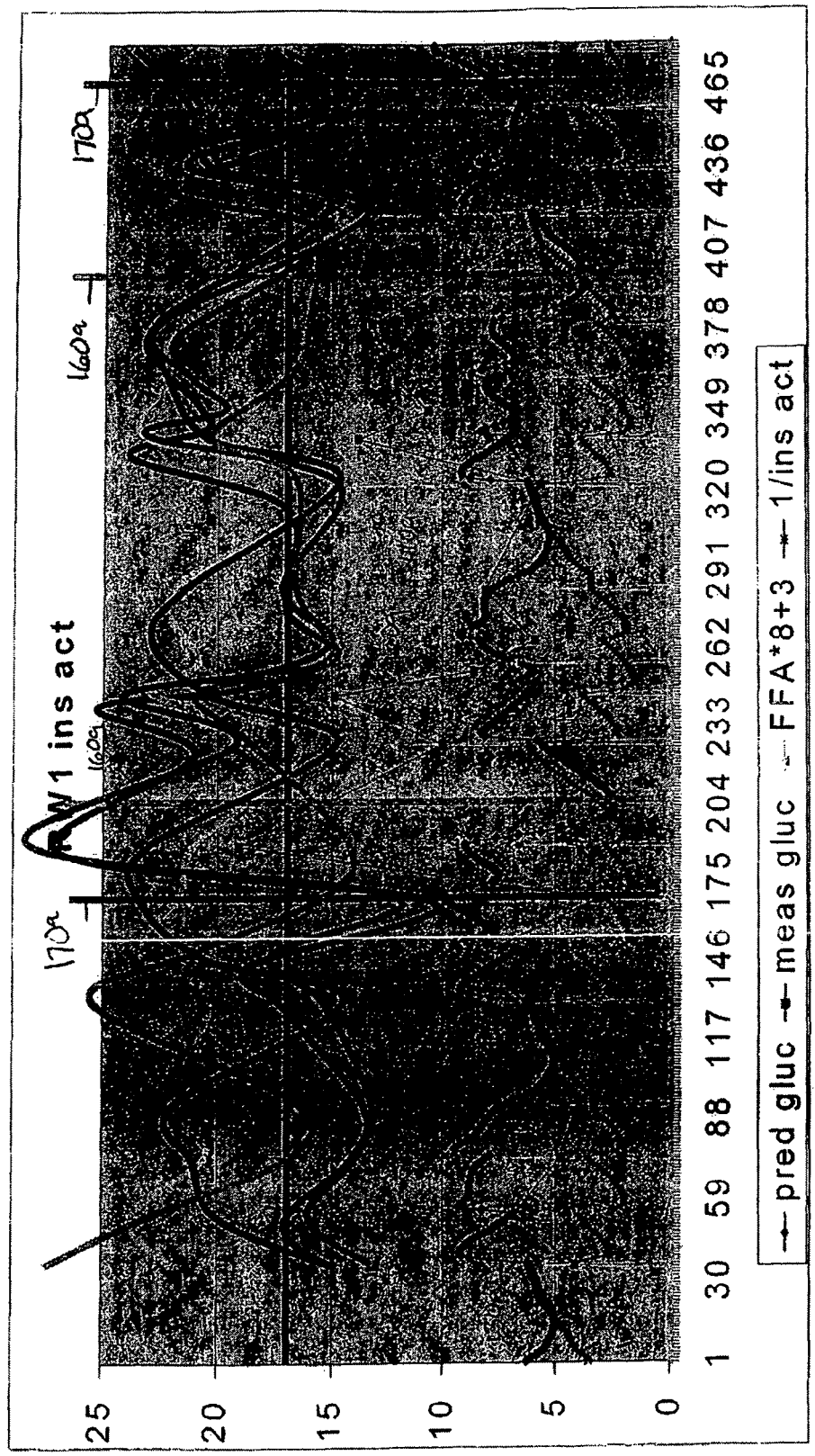
FIG. 12A is a chart illustrating measured results for a patient during a first experiment conducted according to the teachings of the invention.
Figure 12B:
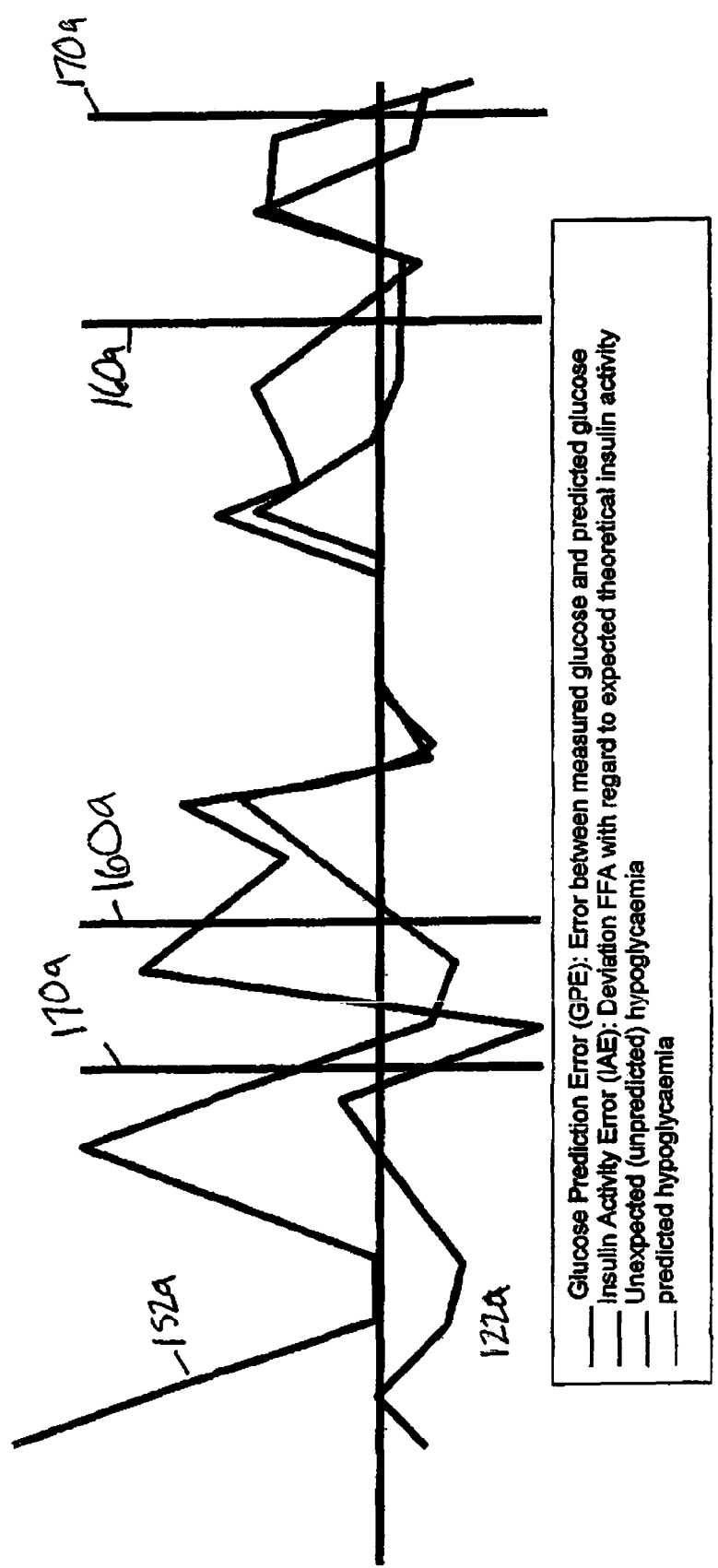
FIG. 12B is a graph showing a glucose prediction error, an insulin activity error, incidents of unexpected hypoglycaemia and incidents of expected hypoglycaemia for the patient during the first experiment.

For example, FIG. 11 shows the display 19 of the health monitoring device according to one embodiment when the device is used to display early morning test results of glucose and IAE. As shown, the display 19 of FIG. 11 displays a first analyte measurement, illustrated as the IAE calculation, and a second analyte measurement, illustrated as the glucose measurement, in measurement region 61. The device compares the measurements to the target range, shown in target region 62. The device may identify the analyte pattern typical for night hypoglycaemia and may provide a diagnosis to the user, shown in diagnosis region 63 of the display 19. For example, as shown, the device may conclude that the patient should reduce his evening insulin to avoid repetition of a night hypoglycaemia, as show by the recommendation 64.

In addition, as a consequence of the negative IAE (high FFA) in the morning, the device may calculate and inform the patient that, for example, 50% more insulin may be needed to tackle the increased insulin resistance, as shown in dosage region 65. However, some modern clinicians may instruct the patient not to increase the insulin dose in this situation of high glucose levels. The negative IAE is primarily due to high counter-regulating hormone activity which will fade over the next 12 hours. The clinician may then want to avoid an excess in insulin activity which may lead to a new hypoglycaemia.

The use of a device that identifies hypoglycaemia retrospectively also provides significant patient benefits. As described, glucose levels alone may not be ideal to dose insulin. Glucose readings can be normal to very high in the morning as a consequence of hypoglycaemia overnight. These patients with high glucose and a negative IAE in the morning should reduce insulin (or increase caloric intake or change meal composition) in the evening rather than the natural reflex of taking more insulin. Current practice in self-dosing of insulin lacks the Real Insulin Activity information and works with theoretical insulin activity alone. As a consequence, the described invention allows patients to avoid the hypoglycaemia overnight by taking the right measures. Instead of the usual several days to get back into control, a patient employing a health monitoring device of the invention may be back on track by the next evening.

The increased insulin resistance in the morning following a hypoglycaemia, as quantified in the IAE can now be used to adjust the insulin dose in the morning. A strong negative IAE indicates a higher amount of insulin will be needed to keep glucose levels within the normal rage. Alternatively, the user may be advised, as modern clinicians now advise, not increase the insulin dose, since the insulin activity error will normalise over the course of the day when the counter-regulating hormones fade out.

Referring again to FIGS. 7A and 7B, the insulin activity error calculated using the device of an illustrative embodiment of the invention may be used to identify over-insulinized patients. The risk exists that the patient may become trapped in a cycle of increasing his insulin each time he perceives a high glucose. Ignorant about the effects of the counter-regulating hormones, a patient may end up with frequent negative IAE's and high glucose while consuming large amounts of insulin, creating a self-perpetuating cycle. The only efficient, though intuitively contrary approach is to drastically reduce the insulin intake to restore the normo-glycemia, reduce the FFA levels and minimize the IAE, which may be advised when employing a device according to the teachings of the invention.

Therefore, the insulin activity error 230 (the difference between the real insulin activity 210 and the theoretical insulin activity 201) as calculated from FFA levels and injected insulin, may provide information early to the patient so he can avoid over-insulinization or restore it.

As shown in FIGS. 7A and 7B, the device 10 of the present invention may be used to track the evolution of the insulin activity error 230. Depending on the volatility of the IAE and the therapeutic goals, the time basis can be changed, showing the evolution over weeks or months 240 rather than days.

An (averaged) intra-day evolution can reveal even more detailed information. Consistent negative IAE's in the late afternoon, for example, may signal to reduce insulin before lunch or increase the lunch calorie content or composition.

According to another embodiment, the calculated insulin activity error may be used as a therapeutic goal. For example, in patients with consistently elevated glucose values and negative IAE, the improvement of the IAE can become a therapeutic objective.

The health-monitoring device 10 of an illustrative embodiment of the present invention may be used to measure and interpret the IAE of a patient, taken at certain moments of the day and at certain intervals, as well as the glucose level of the patient. Based on the measurement of the FFA level, the glucose level and the injected insulin, the device calculates and displays the IAE as shown in FIG. 7B. The progression of the IAE can be displayed in relation to the set therapeutic objective. The objective can be displayed as a progressively tightening zone 250 to allow for flexibility and time to achieve success of the therapy.

In individuals with marginally abnormal glucose values, such as in obesitas or onset metabolic syndrome that do not yet take external insulin, the system and method of the present invention may measure the variable FFA levels only. The system will display the real insulin activity rather than insulin activity error. Therapeutic interventions, such as losing weight, taking insulin sensitizers or any other medication to improve insulin sensitivity, may show a clear improvement of the Real Insulin Activity.

The health monitoring device of the invention may also be used to predict glucose levels more accurately. Glucose prediction algorithms aim at predicting glucose levels based upon the meal, with or without the specifics of the meal composition, the amounts and types of the injected insulin and the glucose values. More complex algorithms also use inputs including, but not limited to, exercise duration and intensity, glycaemic index of the meal, alcohol consumption. By predicting glucose levels, the patient may decide to change his meal intake or quantity of insulin to inject, trying to keep glucose within near-normal levels.

A major draw back of the algorithms used to predict glucose levels in the prior art is that the algorithms use theoretical absorption curves of the injected insulin. These curves try to predict the appearance of insulin in the bloodstream and the insulin activity which is then used in the prediction model. The current prediction algorithms do not take into account other insulin-interfering factors. Such factors include, but are not limited to the variability of the absorption depending on the site of injection or the injection, the effects of the counter-regulating hormones, such as cortisol, catecholamines, growth hormone, glucagons, insulin sensitivity of the various organs, which is mainly driven by the concentration of FFA, the presence and inhibiting actions of anti-insulin antibodies and the variability in the clearance of insulin. For example, absorption may be fast when injected in belly fat, slow when injected in the leg, and scarred tissue may result in retarded absorption.

The illustrative embodiments of the invention, by measuring FFA together with glucose and calculating the insulin activity error, may improve dramatically the accuracy of those algorithms. The invention allows use of the real insulin activity rather than the theoretical insulin activity to increase accuracy.

According to another application, the device 10 utilizes FFA and glucose levels to assess the insulin sensitivity and therefore help in determining an appropriate pre-prandial insulin dose. The combined information of glucose and FFA levels in a patient allow the device 10 to assess the insulin sensitivity of the patient. Information regarding a patient's insulin sensitivity can be particularly relevant when the patient has to inject himself with insulin prior to his meal. The insulin is intended to remove glucose from the bloodstream that appears as a result of the meal digestion. When high levels of FFA are present resulting in a low insulin sensitivity, the user must to inject himself with a higher amount of insulin to avoid high glucose levels after the meal. This is particularly helpful before breakfast when FFA levels are usually high.

According to another application, the health-monitoring device may utilize information regarding FFA and glucose levels for closed loop systems and insulin dosing algorithms. Glucose alone as a reflection of carbohydrate metabolism has proven to be insufficient to build reliable dosing algorithms. Systems based on glucose input alone are lacking the essential information from the fat metabolism, counter-regulating hormones and insulin sensitivity. FFA levels combined with glucose, as set forth in the present invention, provide a more complete picture of the actual metabolic state of the patient. The present invention combines the fat and glucose metabolic information as inputs for insulin dosing algorithms. These algorithms may be stand-alone minicomputer or palmtop based systems as well as incorporated in glucose measurement devices or insulin delivery systems (i.e. insulin pen or pump). Some of those algorithms are predictive in such that they assess the expectable glucose levels in the near future.

Closed loop systems are systems that aim to deliver insulin automatically based on inputs from the patient's metabolic state. They consist typically of a measuring or input device for metabolic parameters (i.e., glucose, dietary input, logging exercise and insulin administration), an insulin dosing algorithm and an insulin delivery system.

EXEMPLIFICATION OF THE INVENTION

A home study was conducted on five diabetic patients (RW, KP, JC, MJ and NO), all type I. The home study was conducted over two separate weeks, during which tests were conducted, tracking insulin levels and glucose levels in the patients' blood. Two diabetic patients (RW and KP) were tested twice, producing two sets of results for these patients.

During testing, Microtainer tubes were used to collect a blood sampled using a finger stick for Free Fatty Acids, b-Hydroxybutyrate. Familiar home monitoring device for glucose testing were used. Sample collection was instructed to be done just before each meal and insulin injection. A fourth sample of the day was taken at bedtime. Samples were then stored by patient at home in the refrigerator. Collection was next morning by taxi service for appropriate storage in the lab and analysis.

FIGS. 12A-18B are graphs shown the results of the tests done for each test involving a patient. FIGS. 12A, 13A, 14A, 15A, 16A, 17A and 18A illustrate the results for each patient, with FIG. 13A representing the second testing of patient "RW" and FIG. 15A representing the second testing of patient "KP". FIGS. 12B, 13B, 14B, 15B, 16B, 17B and 18B are charts diagramming the glucose prediction error and insulin activity error based on the test results for each patient.

In addition to providing blood samples, patients registered carbohydrate intake and insulin injections. The carbohydrate intake and insulin injections were used to construct a glucose prediction curve 130a-130g, shown in FIGS. 12A, 13A, 14A, 15A, 16A, 17A and 18A, according to the algorithm of DIASnet. The generated glucose prediction curves show expected glucose values based on the theoretical action profiles of the injected insulin.

The error between the predicted glucose and measured glucose was defined graphically as lines 122a-122g, shown in FIGS. 12B, 13B, 14B, 15B, 16B, 17B and 18B. In addition, the unexplained difference between FFA and pre-prandial insulin levels was defined graphically, as shown by lines 152a-152g in FIGS. 12B, 13B, 14B, 15B, 16B, 17B and 18B.

Figure 13A:
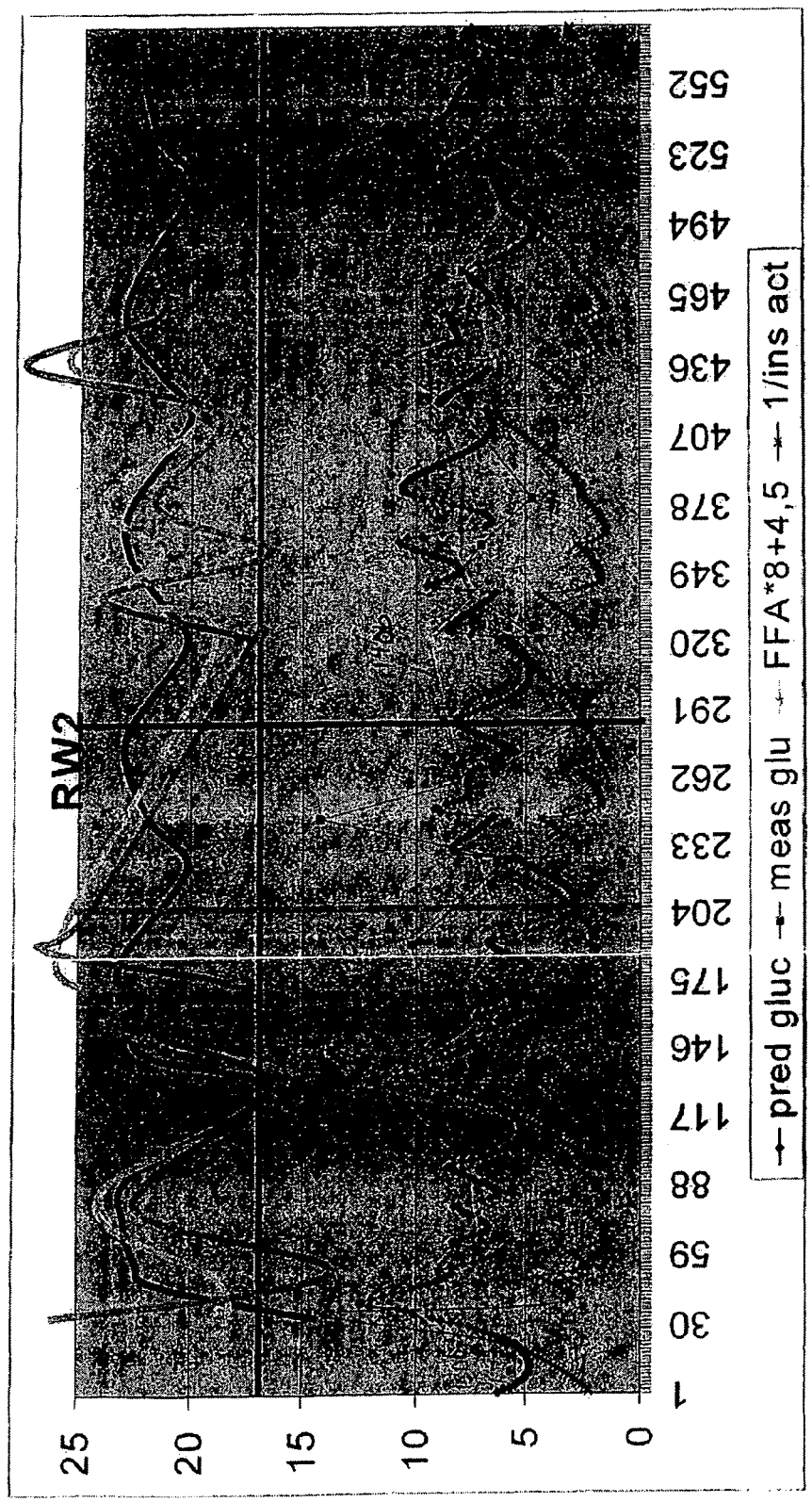
FIG. 13A is a chart illustrating measured results for a patient during a second experiment conducted according to the teachings of the invention.
Figure 14A:
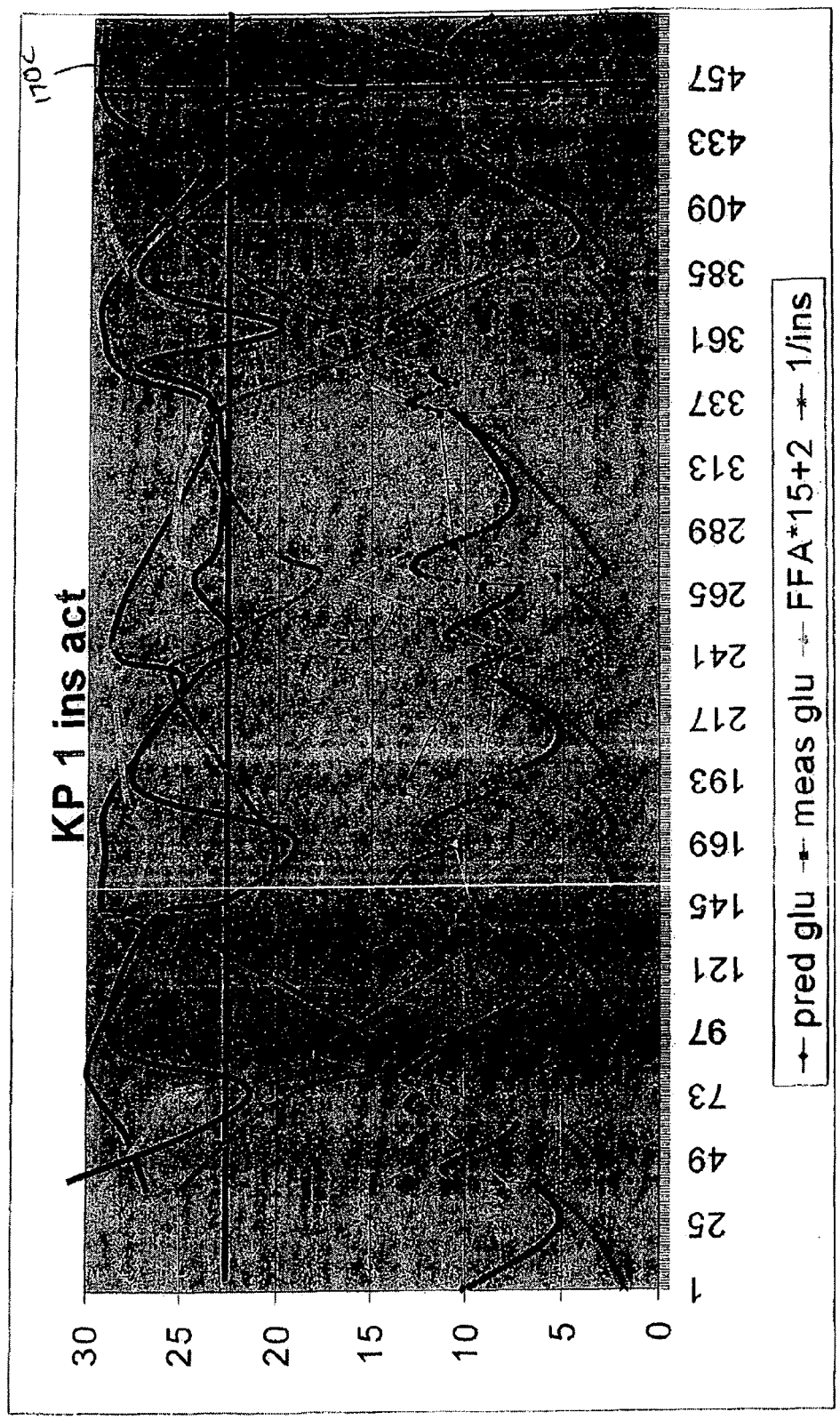
FIG. 14A is a chart illustrating measured results for a patient during a third experiment conducted according to the teachings of the invention.
Figure 14B:
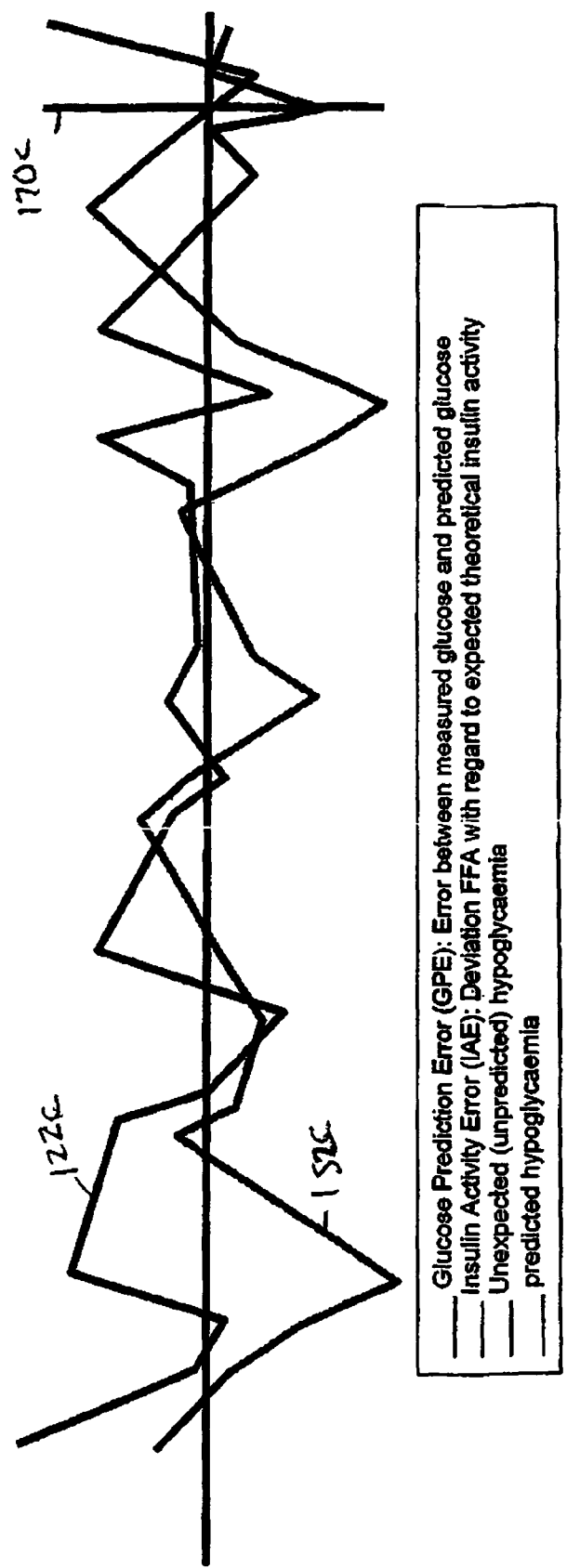
FIG. 14B is a graph showing a glucose prediction error, an insulin activity error, incidents of unexpected hypoglycaemia and incidents of expected hypoglycaemia for the patient during the third experiment.
Figure 15A:
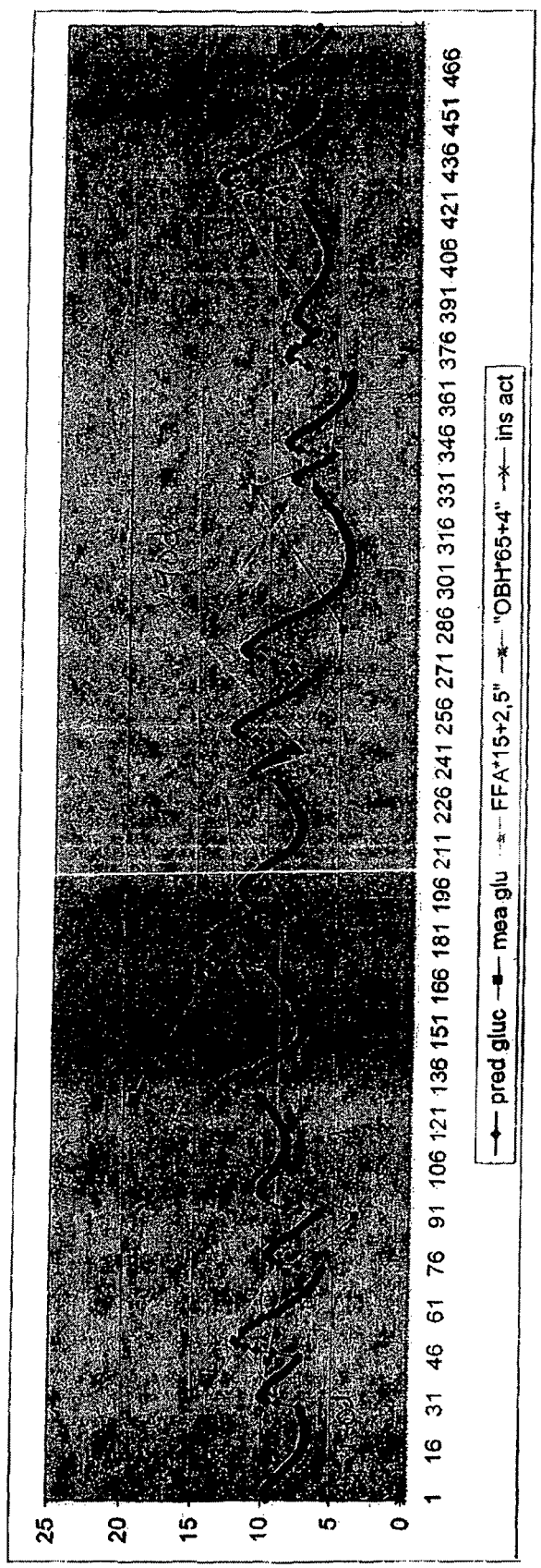
FIG. 15A is a chart illustrating measured results for a patient during a fourth experiment conducted according to the teachings of the invention.
Figure 16A:
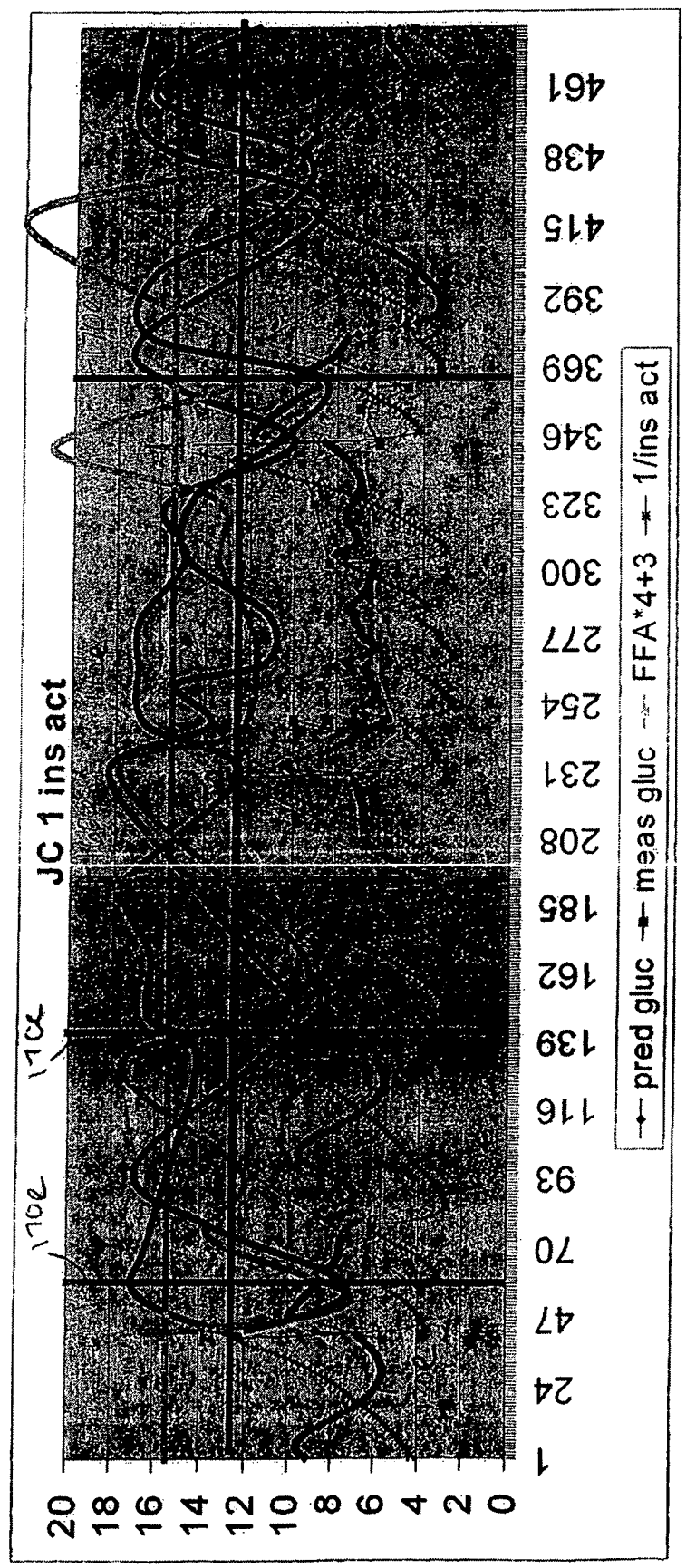
FIG. 16A is a chart illustrating measured results for a patient during a fifth experiment conducted according to the teachings of the invention.
Figure 17A:
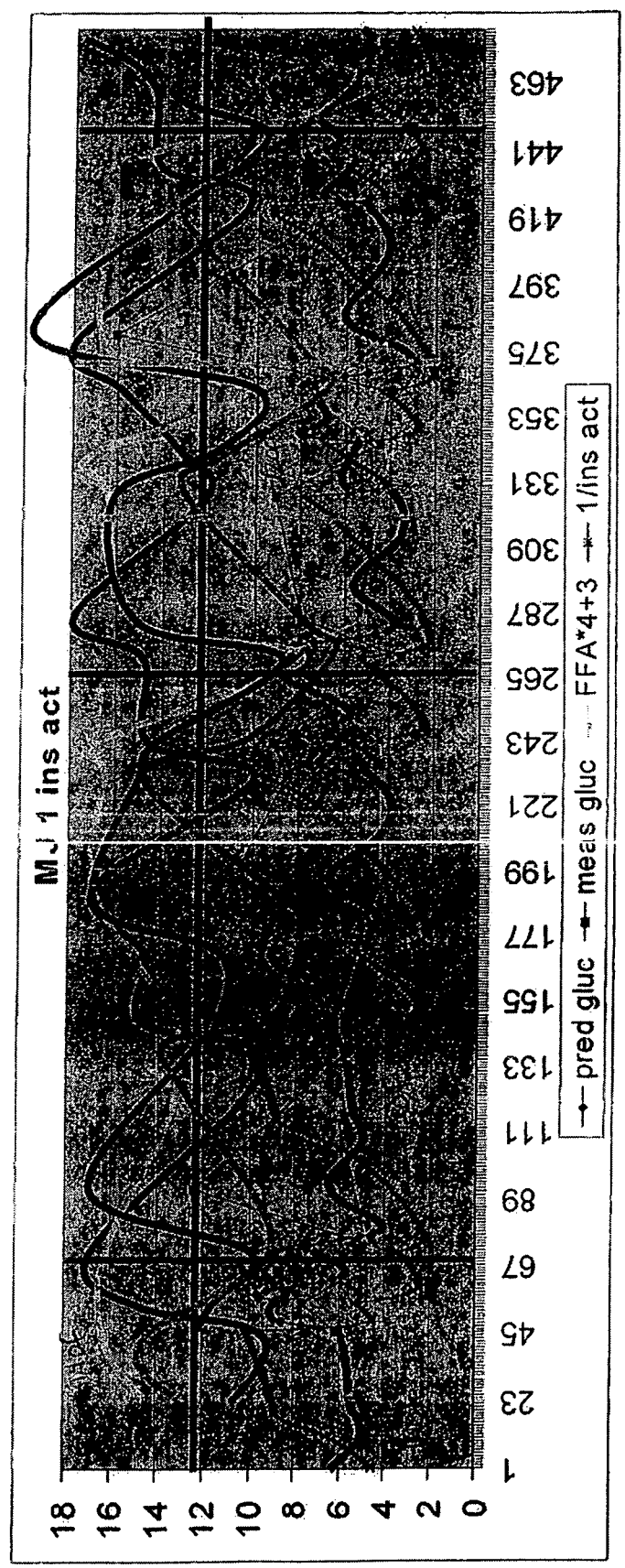
FIG. 17A is a chart illustrating measured results for a patient during a sixth experiment conducted according to the teachings of the invention.
Figure 17B:
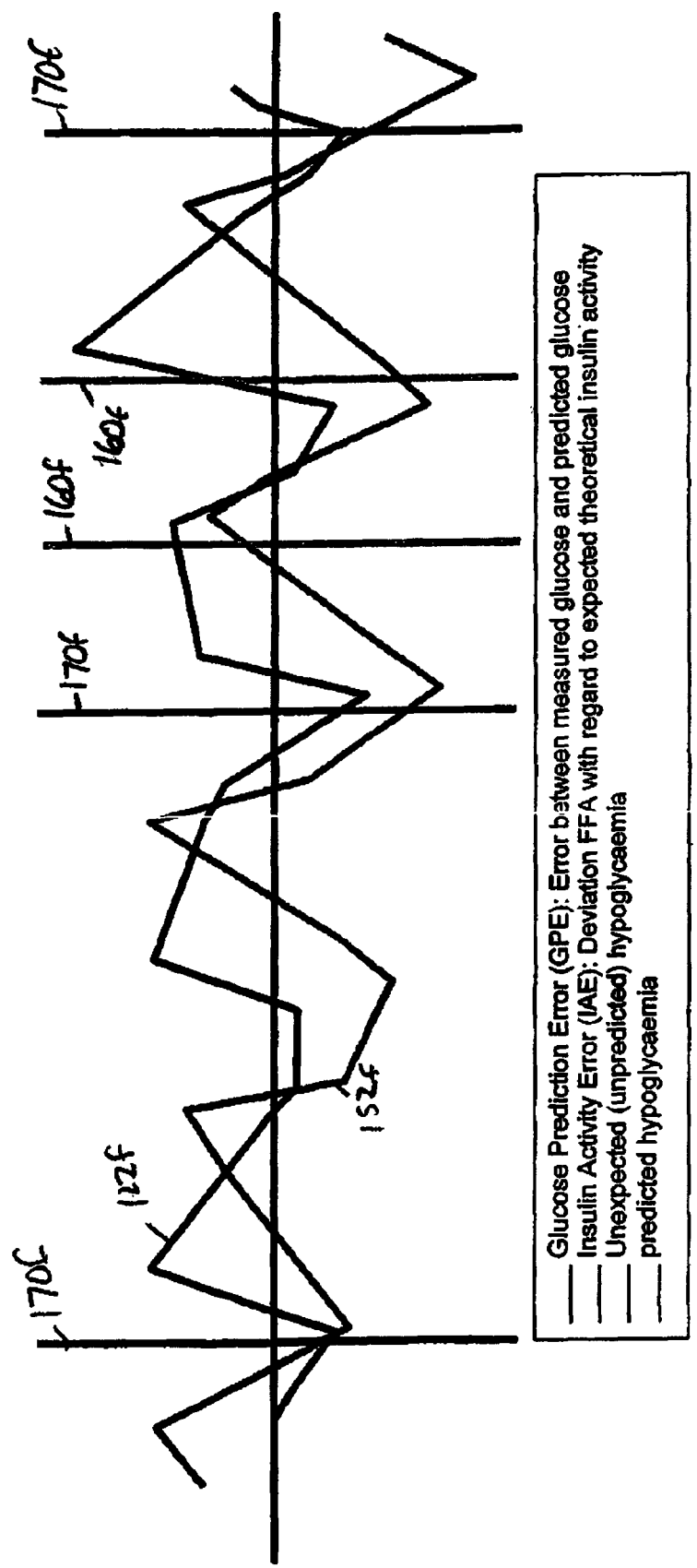
FIG. 17B is a graph showing a glucose prediction error, an insulin activity error, incidents of unexpected hypoglycaemia and incidents of expected hypoglycaemia for the patient during the sixth experiment.
Figure 18A:
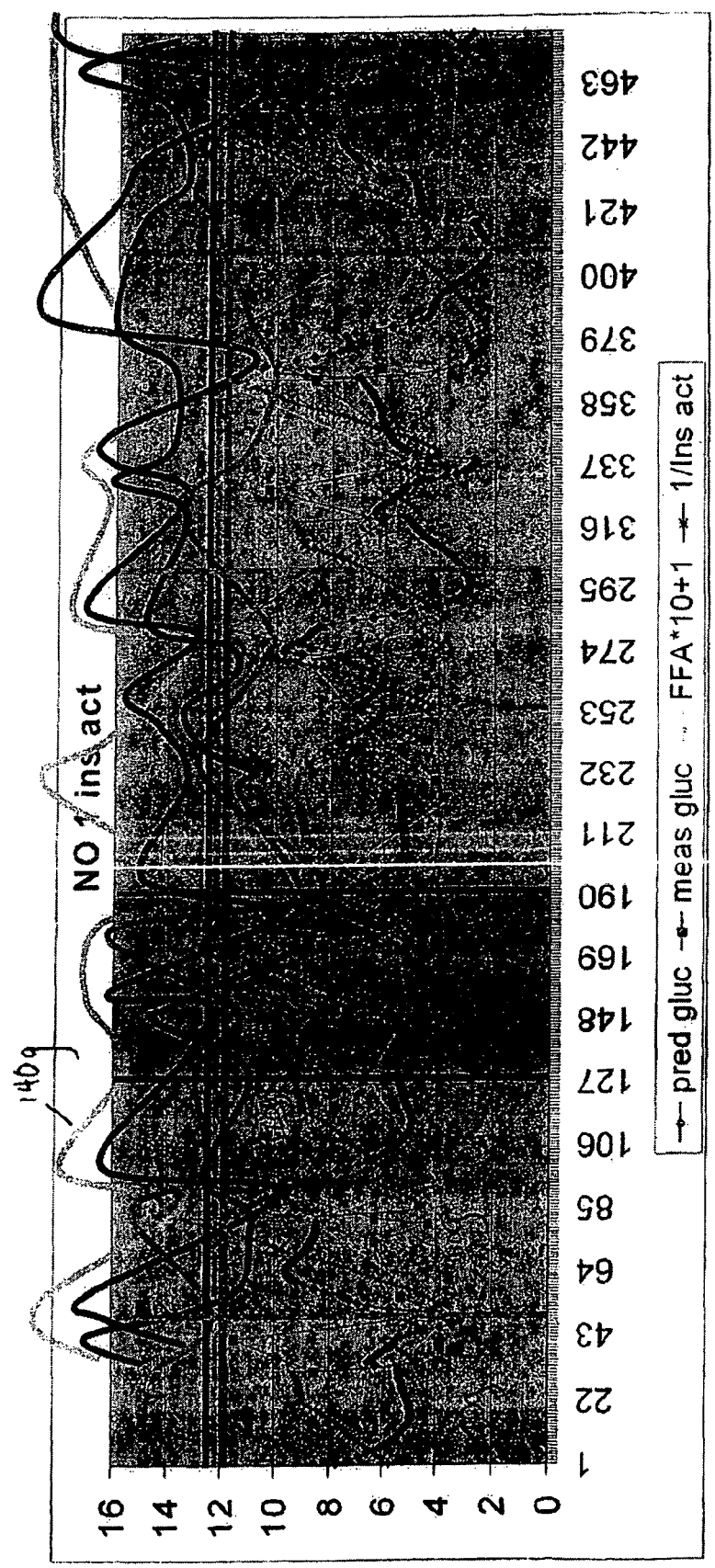
FIG. 18A is a chart illustrating measured results for a patient during a seventh experiment conducted according to the teachings of the invention.
Figure 18B:
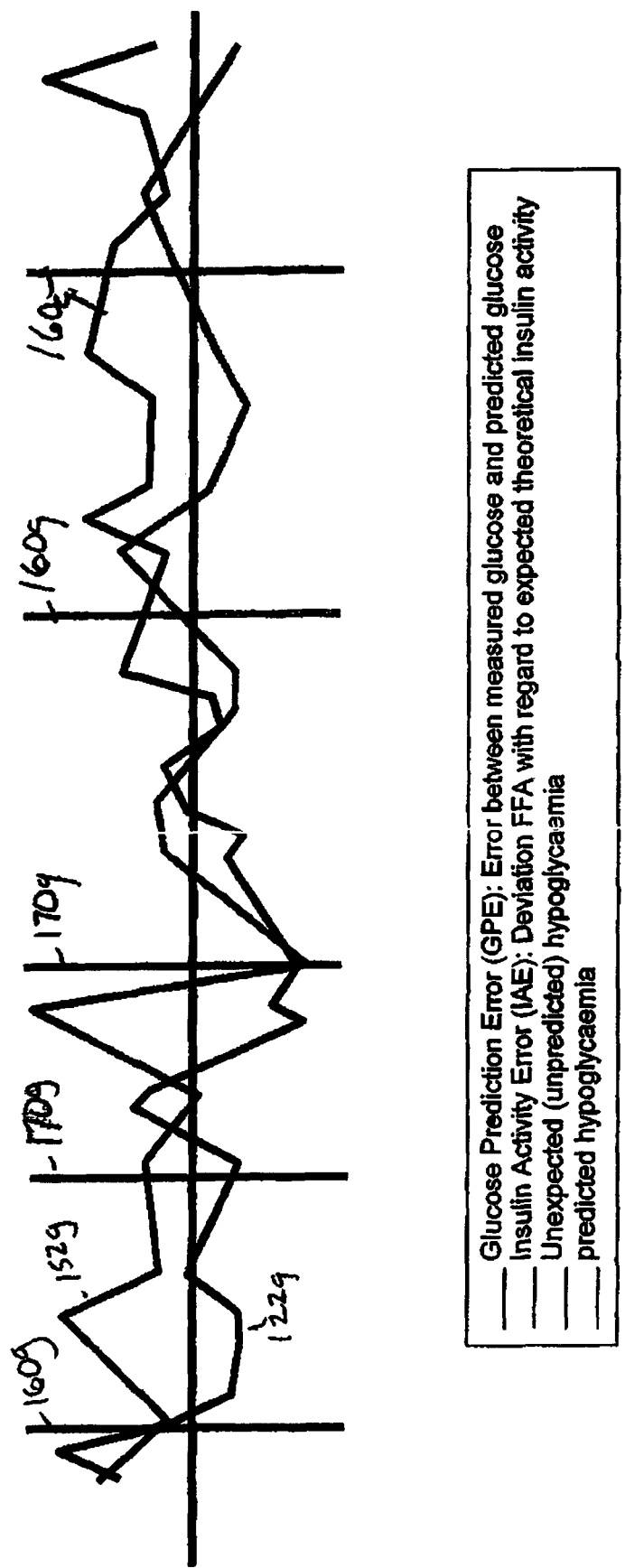
FIG. 18B is a graph showing a glucose prediction error, an insulin activity error, incidents of unexpected hypoglycaemia and incidents of expected hypoglycaemia for the patient during the seventh experiment.

The measured glucose levels (lines 120a-g, respectively), the predicted glucose levels (lines 130a-g, respectively), the free fatty acid levels (lines 140a-g, respectively) and the insulin activity levels (lines 150a-g, respectively) were charted for each patient over the testing period. FIGS. 12A, 13A, 14A, 15A, 16A, 17A and 18A illustrate the results for each patient, with FIG. 13A representing the second testing of patient "RW" and FIG. 15A representing the second testing of patient "KP". FIGS. 12B, 13B, 14B, 15B, 16B, 17B and 18B chart the glucose prediction error (lines 122a-g, respectively), the insulin activity error (lines 152a-g, respectively), the incidents of predicted hypoglycaemia (lines 160a-g, respectively) based on the measurements of glucose levels using traditional methods, free fatty acid levels and insulin activity levels, and the incidents of unexpected or unpredicted hypoglycaemia (lines 170a-e, respectively) that occurred during each study.

The glucose prediction error curve 122a-g charts the error between the measured glucose and the predicted glucose during each testing period for each patient, respectively. The insulin activity error curve 152a-g charts the deviation of the free fatty acid levels with regard to expected theoretical insulin activity for each testing period for each patient, respectively. During an analysis, the peaks in the insulin activity error were compared with the effect on the glucose prediction error. It was found that strong negative glucose prediction errors were usually preceded by strong positive peaks in the insulin activity error curve. When the predicted glucose was already low, they typically lead to hypoglycaemia.

As illustrated in the summary charts, in FIGS. 12B, 13B, 14B, 15B, 16B, 17B and 18B, an unexpected hypoglycaemia incident is typically preceded (up to 6 hours in advance) by a positive Insulin-Activity-Error (IAE). This is also valid for any negative glucose prediction error (GPE). Conversely, a positive GPE is usually preceded by a negative IAE. The health-monitoring device 10 of the illustrative embodiments of the invention may utilize this tracking to promote and improve the user's health.

As also shown in the summary charts, there are two hypoglycaemic events possible: the predicted hypoglycaemic events, indicated by lines 160a-g and the unpredicted hypoglycaemic events, indicated by lines 170a-g. The predicted hypoglycaemic events 160a-g usually result from injecting too much insulin or eating too little, and are easy to prevent by looking at the prediction curve and take appropriate pre-emptive action, such as eating more or injecting less. The unpredicted hypoglycaemic events 170a-g result from too much insulin activity liberated from the injection site earlier than expected (accelerated release) or later and more than expected (retarded release with accumulation of the previous injection dose). The unpredicted hypoglycaemic events 170a-g can also result when pre-existing insulin resistance or counter-regulating hormone activity can have faded.

The curves show that most hypoglycaemic and hyperglycaemic events are unpredicted by the prediction curves of traditional models.

In addition, hyperglycaemic events that may be caused by too little Insulin activity or excess in counter-regulating hormones and/or insulin resistance (which is to the greater part caused by the high FFA levels), are also often unpredicted.

A positive IAE (more suppressed lipolysis with low FFA's than explainable by the theoretical insulin absorption curves) may lead to a negative GPE (lower glucose levels than predicted) within 4-6 hours. Similarly, less than expected insulin activity can lead to higher than predicted glucose levels.

The illustrative embodiment of the invention employs these results to increase the accuracy of traditional glucose prediction algorithms. The results may be explained through the interaction between different hormones. Lipolysis is under the control of the same hormones as carbohydrate metabolism. Fat tissue is very sensitive to the actions of insulin. Meals do not affect FFA levels in the same way that they alter glucose levels. Insulin, glucagon, growth hormone, adrenergic hormones, and other hormones all regulate in a combined fashion lipolysis. The results show that FFA levels are reliable for assessing the effective insulin activity. The absorption of the insulin depot at the injection site is highly variable and rather unpredictable, especially the longer the action profile of the insulin is. FFA levels give a more accurate picture of the combine hormonal activity (including the insulin resistance) than the assumed theoretical absorption curves. Currently, by testing glucose alone, the hypoglycaemic (and hyperglycaemic) episodes are usually not predictable. Using the method of testing FFA and Glucose in accordance with the teachings of the invention enables detection of over or under activity of insulin and counter regulating hormones which may lead to hypo- or hyperglycaemia.

The examples confirm that the invention is far more accurate in predicting hyper- and hypo-glycaemia. Correcting a traditional glucose prediction algorithm with this invention predicted twice as many hypoglycaemic episodes than would be predicted using traditional algorithms.

Therefore, the invention facilitates monitoring, treatment, management and improvement of the overall health of a user by allowing a user to more accurately control glucose levels, assess a real insulin activity level of the user, track an insulin activity error, be warned about imminent hypoglycaemia or hyperglycaemia, receive formulated insulin dosage from the device, receive advice from the device and so on.

The present invention has been described relative to an illustrative embodiment. Since certain changes may be made in the above constructions without departing from the scope of the invention, it is intended that all matter contained in the above description or shown in the accompanying drawings be interpreted as illustrative and not in a limiting sense.

It is also to be understood that the following claims are to cover all generic and specific features of the invention described herein, and all statements of the scope of the invention which, as a matter of language, might be said to fall therebetween.

What is claimed is:

1. A computer-implemented method of assessing an insulin activity error and its effect on glucose levels, the method comprising the computer-implemented steps of:
    measuring an amount of a fat metabolism analyte in a biological fluid sample and an amount of a glucose metabolism analyte in the biological fluid sample,
    determining, using a computer, a real insulin activity level, wherein the real insulin activity level comprises a reciprocal conversion of the amount of the fat metabolism analyte in the biological fluid sample,
    comparing, using the computer, the real insulin activity level with a theoretical insulin activity level to calculate the insulin activity error; and
    predicting, using the computer, a prospective glucose level using the amount of the glucose metabolism analyte in the biological fluid and the calculated insulin activity error,
    wherein a positive insulin activity error is predictive of a glucose level which is lower than that predicted by the theoretical insulin activity level, and
    wherein a negative insulin activity error is predictive of a glucose level which is higher than that predicted by the theoretical insulin activity level.

2. The method of claim 1, wherein the fat metabolism analyte is selected from the group consisting of ketones, glycerol, free fatty acids and a fatty acid indicative of free fatty acid levels.

3. The method of claim 1, wherein the glucose metabolism analyte is selected from the group consisting of glucose, pyruvate, glucose-6-phosphate and lactate.

4. The method of claim 1, wherein the sample comprises one of blood, a derivate of blood, interstitial fluid, urine and saliva.

5. The method of claim 1, wherein the step of predicting a prospective glucose level comprises predicting a likelihood of a user developing one of hypoglycaemia and hyperglycaemia.

6. The method of claim 1, wherein the method comprises a retrospective diagnosis of one of hypoglycaemia and hyperglycaemia.

7. The method of claim 1 wherein the method comprises recommending a timing for a future determination of analyte levels in a user.

8. A computer-implemented method of predicting a user's glucose levels in the future, the method comprising the computer-implemented steps of:
    measuring an amount of a fat metabolism analyte in a biological fluid sample and an amount of a glucose metabolism analyte in the biological fluid sample,
    determining, using a computer, a real insulin activity level in the user, wherein the real insulin activity level comprises a reciprocal conversion of the amount of the fat metabolism analyte in the biological fluid sample;
    comparing, using the computer, the real insulin activity level with a theoretical insulin activity level to calculate an insulin activity error; and
    running, using the computer, a glucose prediction algorithm corrected for the insulin activity error, wherein the correction comprises decreasing a glucose level predicted by the theoretical insulin activity when the insulin activity error is positive and increasing a glucose level predicted by the theoretical insulin activity when the insulin activity error is negative, the algorithm taking into consideration an additional parameter comprising at least one of: body mass index, gender, meal intake, medication, exercise duration and intensity, alcohol consumption and weight.

9. The method of claim 8, further comprising the step of:
    calculating, using the computer, a likelihood of the user developing one of hypoglycaemia and hyperglycaemia.

10. The method of claim 8, further comprising the step of: calculating, using the computer, a likelihood of one of a past hypoglycaemia incident and a past hyperglycaemia incident.

11. The method of claim 8, further comprising the step of: formulating test frequency advice to the user.

12. The method of claim 8, further comprising the step of: formulating medication dosing advice to the user.

13. The method of claim 8, further comprising the step of: automatically communicating insulin dose information to an insulin delivery device.

14. A health-monitoring device comprising:
a test element configured to receive a biological fluid sample and measure:
an amount of a fat metabolism analyte in the biological fluid sample, and
an amount of a glucose metabolism analyte in the biological fluid sample;
a processor programmed to:
assess a real insulin activity level of a user, wherein the real insulin activity level comprises a reciprocal conversion of the amount of the fat metabolism analyte in the biological fluid sample,
compare the real insulin activity level with a theoretical insulin activity level to calculate an insulin activity error, and
predict a prospective glucose level using the amount of the glucose metabolism analyte in the biological fluid and the calculated insulin activity error,
wherein a positive insulin activity error is predictive of a glucose level which is lower than that predicted by the theoretical insulin activity level, and
wherein a negative insulin activity error is predictive of a glucose level which is higher than that predicted by the theoretical insulin activity level; and
a display device for displaying the real insulin activity level, the insulin activity error, or the prospective glucose level.

15. The device of claim 14, wherein the test element comprises one or more of a photometric, reflectometric, electrochemical and fluorescence based system for analyzing the biological fluid sample.

16. The device of claim 14, wherein a single test element measures both an amount of a fat metabolism analyte in the biological fluid sample and an amount of a glucose metabolism analyte in the biological fluid sample.

17. The device of claim 14, wherein the device automatically or continuously measures the glucose metabolism analyte.

18. The device of claim 14, wherein the device automatically or continuously measures the fat metabolism analyte.

19. The device of claim 14, further comprising:
a memory element for tracking the evolution of one of the real insulin activity level and the insulin activity error for the user.

20. The method of claim 1, wherein the fat metabolism analyte is a ketone and the glucose metabolism analyte is glucose.

21. The method of claim 1, wherein the biological fluid sample is an extracted biological fluid sample.

22. The device of claim 14, wherein the test element comprises an electrochemical based system for analyzing the biological fluid sample.

23. The device of claim 22, wherein the test element comprises a test strip.

24. The device of claim 14, wherein the test element comprises a test strip.

25. The device of claim 16, wherein the test element comprises a test strip.

26. The device of claim 14, wherein the test element comprises a skin-inserted device.

27. The device of claim 14, wherein the test element comprises a non-invasive measurement device.

28. The method of claim 8, wherein the measuring is performed with a test element configured to contact the biological fluid sample.

29. The method of claim 28, wherein the test element comprises a test strip.

30. The method of claim 29, wherein the test strip is an electrochemical-based test strip.

31. The method of claim 30, wherein the test strip is configured to measure both the amount of the fat metabolism analyte and the amount of the glucose metabolism analyte.

32. The method of claim 28, wherein the test element comprises a skin-inserted device.

33. The method of claim 28, wherein the test element comprises a non-invasive measurement device.

* * * * *

UNITED STATES PATENT AND TRADEMARK OFFICE
CERTIFICATE OF CORRECTION

| | | |
|---|---|---|
| PATENT NO. | : 8,718,943 B2 | Page 1 of 1 |
| APPLICATION NO. | : 11/528997 | |
| DATED | : May 6, 2014 | |
| INVENTOR(S) | : Moerman | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1021 days.

Signed and Sealed this
Twenty-eighth Day of June, 2016

Michelle K. Lee
*Director of the United States Patent and Trademark Office*